United States Patent [19]

Strickland et al.

[11] Patent Number: 5,130,143
[45] Date of Patent: Jul. 14, 1992

[54] USE OF A LOW AFFINITY-HEPARIN FRACTION IN CONJUNCTION WITH T-PA FOR THROMBOLYTIC THERAPY

[75] Inventors: Sidney Strickland, Setauket; Patricia Andrade-Gordon, East Setauket, both of N.Y.

[73] Assignee: The Research Foundation of State University of New York, Albany, N.Y.

[21] Appl. No.: 267,499

[22] Filed: Nov. 4, 1988

[51] Int. Cl.⁵ .............. A61K 37/547; A61K 31/725; C12N 11/04; C08B 37/10
[52] U.S. Cl. .................... 424/94.64; 424/94.63; 544/56; 435/178; 435/219; 435/226; 536/21
[58] Field of Search .......... 435/178, 219, 226; 514/56; 536/21; 424/94.63, 94.64

[56] References Cited

U.S. PATENT DOCUMENTS

| | | | |
|---|---|---|---|
| 4,119,774 | 10/1978 | Andersson et al. | 536/21 |
| 4,687,765 | 8/1987 | Vairel et al. | 514/56 |
| 4,745,180 | 5/1988 | Moreland et al. | 514/56 |
| 4,751,084 | 1/1989 | Feder et al. | 424/94.64 |
| 4,752,603 | 2/1989 | Collen et al. | 514/21 |
| 4,753,879 | 2/1989 | Rosa et al. | 435/172.3 |
| 4,777,161 | 10/1988 | Lormeau et al. | 514/56 |
| 4,847,338 | 7/1989 | Linhardt et al. | 536/54 |

OTHER PUBLICATIONS

Stassen et al., Thromb. Haemostasis, 58(3) 947–950 (8/87).

deProst, "Heparin fractions and analogues: a new therapeutic possibility for thrombosis", TIPS, 496–500 (Dec. 1986).

Castellot, Jr., et al., "Structural Determinants of the Capacity of Heparin, to Inhibit the Proliferation of Vascular Smooth Muscle Cells. II. Evidence for a Pentasaccharide Sequence That Contains a 3-O-Sulfate Group", The Journal of Cell Biology, 102, 1979–1989 (1986).

Shively et al., "Formation of Anhydrosugars in the Chemical Depolymerization and Heparin", Biochemistry, 15, 3932–3962 (1976).

Barrowcliffe et al. "An International Standard for Low Molecular Weight Heparin", Thrombosis and Haemostais, 60, 1–7 (1988).

Teien, et al., "Anticoagulant Activity of Heparin: Assay of Bovine, Human and Porcine Preparations by Amidolytic and Clotting Methods", Throm. Res., 11, 107–117 (1977).

Verstraete, et al., Blood, 67, 1529 (1986).

Hoylaerts et al., J. Biol. Chem., 257, 2912 (1982).

Collen et al., Circulation, 70, 1012 (1984).

The TIMI Study Group, New England Journal of Medicine, 312, 932 (1985).

Verstraete, M. et al., Lancet 1, 842 (1985).

Verstraete, M. et al., Lancet 2, 965 (1985).

Vinazzer et al., Influence of heparin; of Different Heparin Fractions and of a Low Molecular Weight Heparin-Like Substance on the Mechanisms of Fibrinolysis, Throm. Res., 27, 341 (1982).

Turpie, et al., A Randomized Controlled Trail of a Low-Molecular-Weight Heparin (Exoxaparin) to prevent Deep-Vein Thrombosis in Patients Elective Hip Surgery, New England Journal of Medicine, 315, 925–929 (1986).

Sherry, Tissue Plasminogen Activator (t-PA) Will It Fulfill Its Promise? New England Journal of Medicine, vol. 13, No. 16, 1014–1017 (1985).

(List continued on next page.)

Primary Examiner—Jacqueline Stone
Attorney, Agent, or Firm—Hoffmann & Baron

[57] ABSTRACT

A composition for thrombolytic therapy includes a tissue-type plasminogen activator (t-PA) and a low affinity heparin fraction. The composition is administered intravenously to allow the t-PA to dissolve blood clots while the low affinity heparin fraction prevents reocculsion without the harmful side effects observed for unfractionated heparin, such as, stimulation of and interference with t-PA activity in the circulatory system, as well as, interference with fibrinolytic activity which can cause hemorrhaging in the mammalian circulatory system.

4 Claims, 26 Drawing Sheets

OTHER PUBLICATIONS deProst, Heparin Fractions and Analogues: A New Therapeutic Possibility for Thrombosis, Trends in Pharmacological Sciences, 7, 496–500 (Dec. 1986).

Paques et al., Study on the Mechanism of Action of Heparin and Related Substances on the Fibrinolytic System: Relationship Between Plasminogen Activators and Heparin, Thrombosis Research 42, 797–807 (1986).

Bratt et al., Thromb. Haemostasis, 53, 298–211 (1985).

Andrade-Gordon, P., and Strickland, S., Interaction of Heparin with Plasminogen Activators and Plasminogen: Effects on the Activation of Plasminogen Biochem. 25, 4033 (1986).

Andrade-Gordon, P. and Strickland, S., New Strides in Immediate Treatment for Heart Attacks, Biotechnology Network, a newsletter of the State University of New York at Stony Brook (May/Jun. 1987).

Deutsch et al., Science, 170, 1095–1096 (1970).

Dane and Reich, Proteases and Biological Control, 356, edited by Reich et al., Cold Spring Harbor Laboratory, NY (1975).

Verheijen et al., Thromb. Res. 32, 87–92 (1983).

Markwell et al., Biochemistry, 17, 4807–4817 (1978).

Robbins, et al. Methods Enzymol., 19, 184–199 (1970).

Laemmli, Nature (London), 227, 680–685 (1970).

Rosenberg et al., J. Biol. Chem. 248, 6490–6505 (1973).

Teien et al., Thromb. Res. 11, 107–117 (1977).

Granelli-Piperno, et al., J. Exp. Med., 148, 223–234 (1978).

Belin et al., EMBO J. 3, 1901–1906 (1984).

Smith, et al., Analytical Biochemistry, 109, 466–473 (1980).

Danishefsky et al., in Biochem. Biophys. Acta, 101, 37–45 (1965).

Vassalli, et al., J. Exp. Med. 150, 1653–1668 (1984).

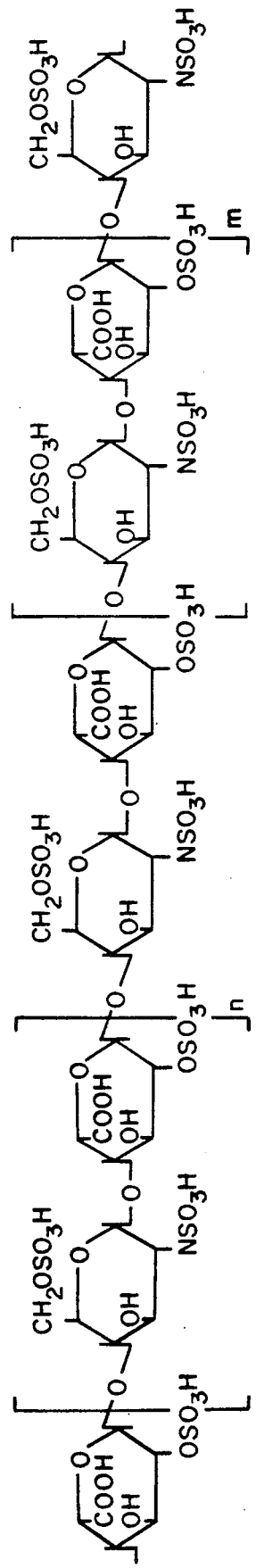
FIG. 2  STRUCTURE OF HMW HEPARIN:

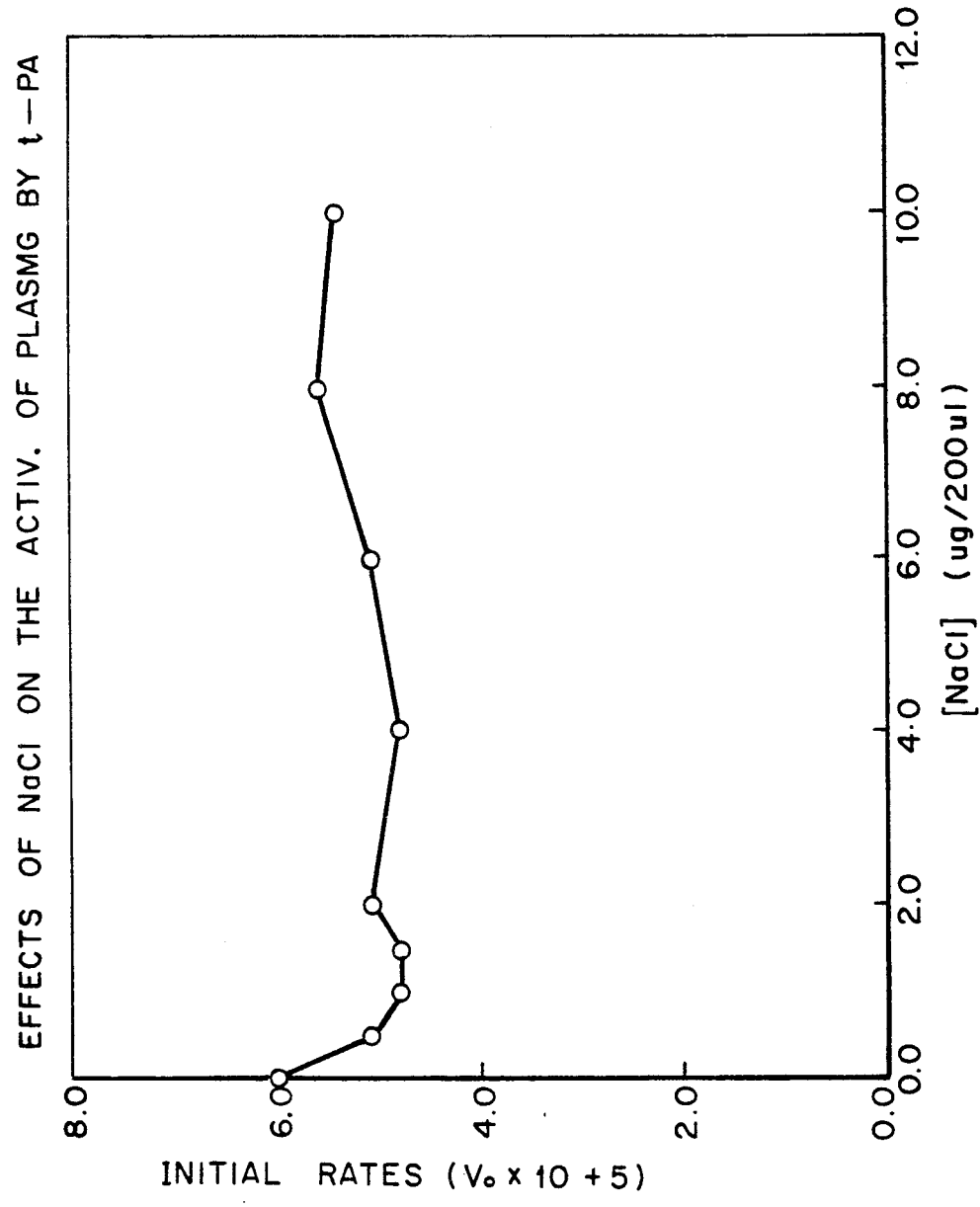

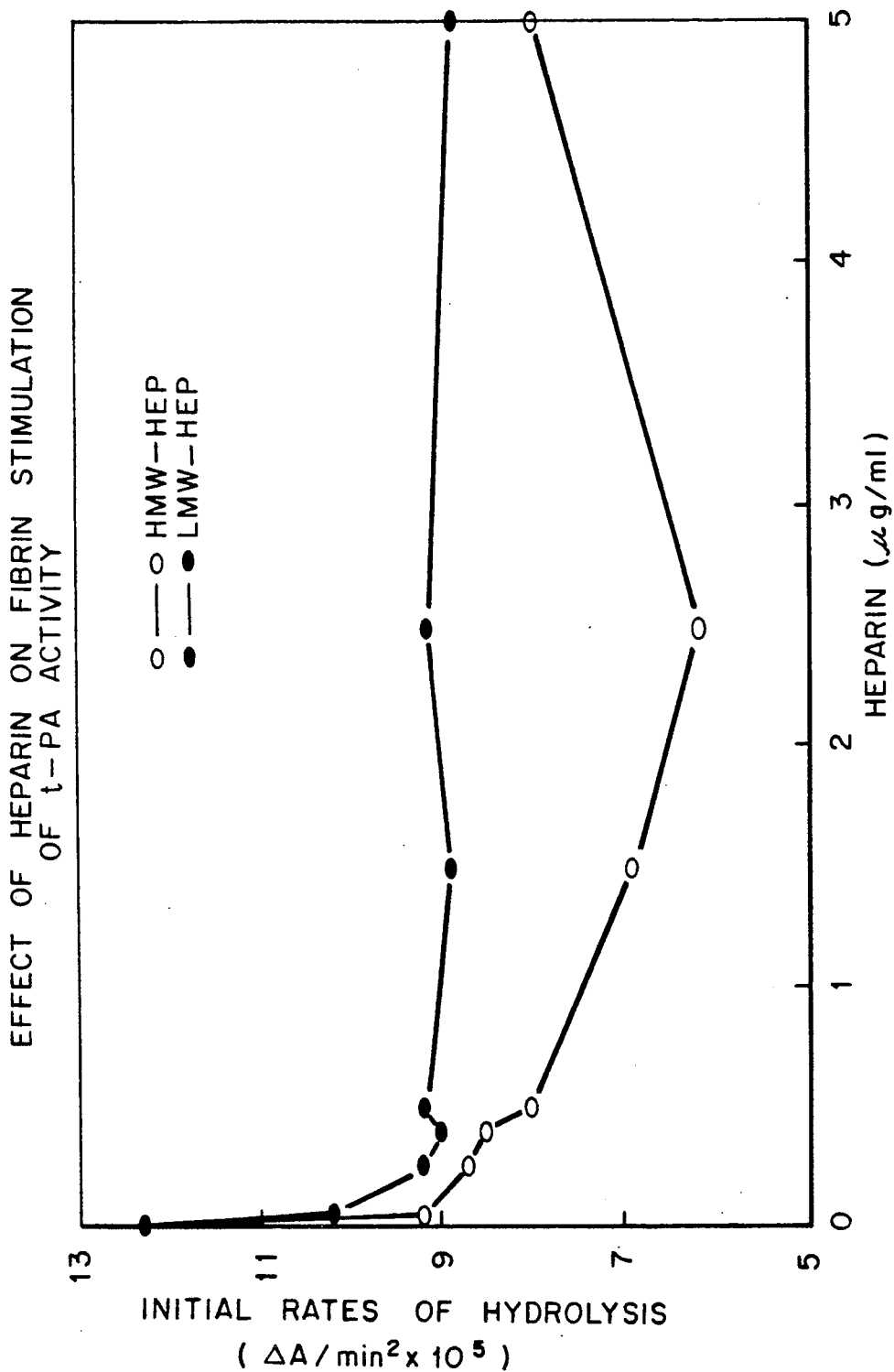

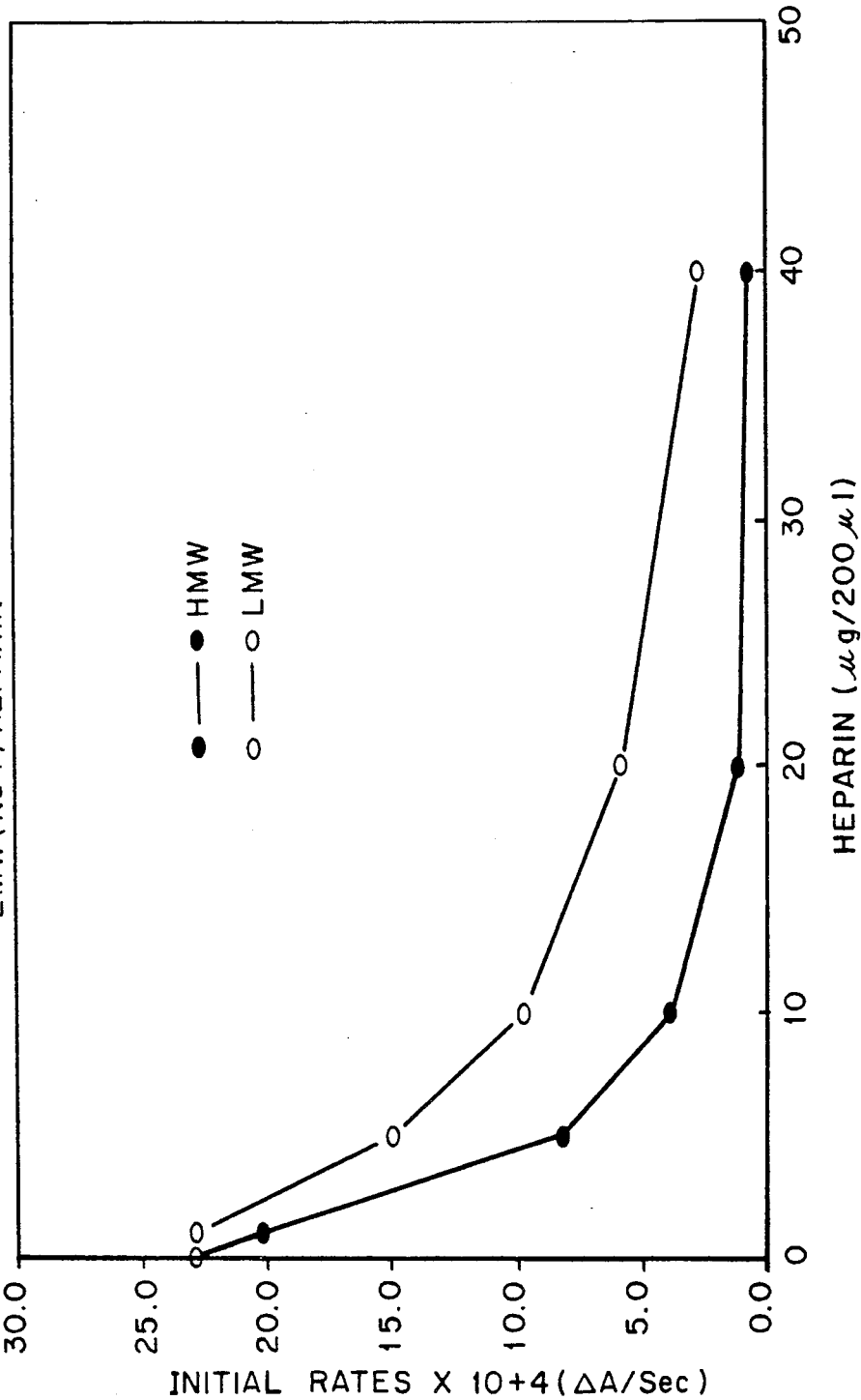

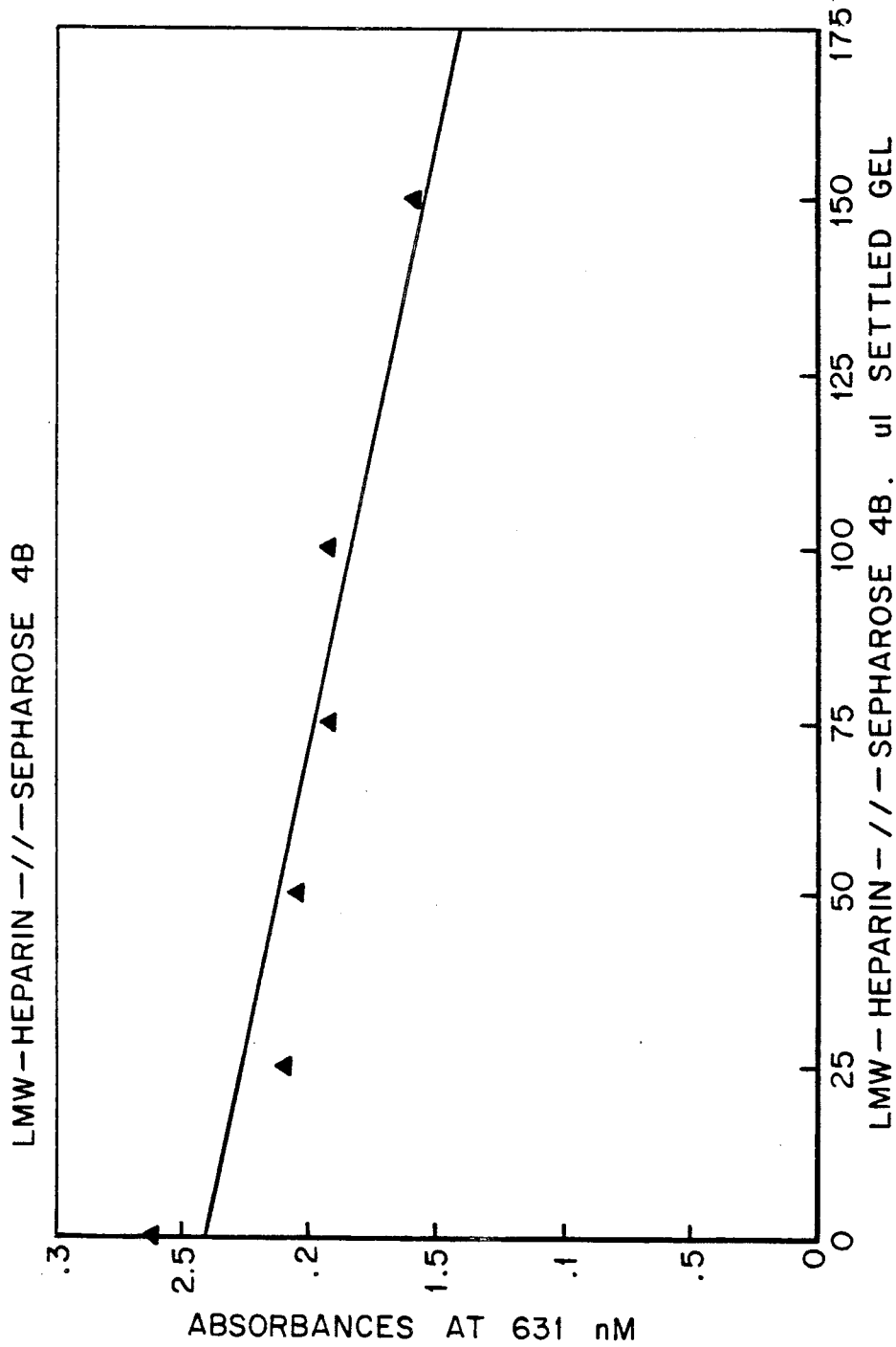

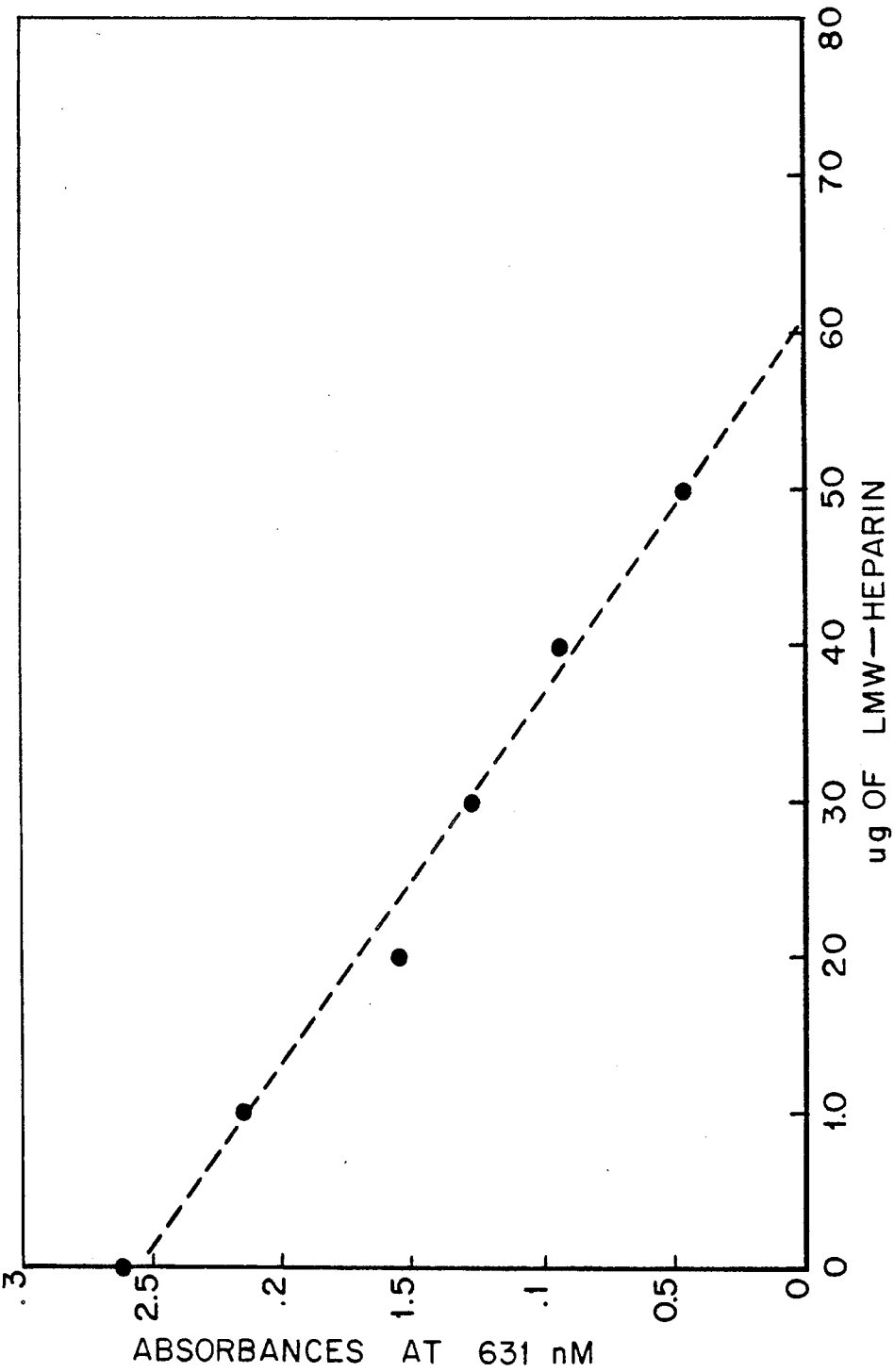

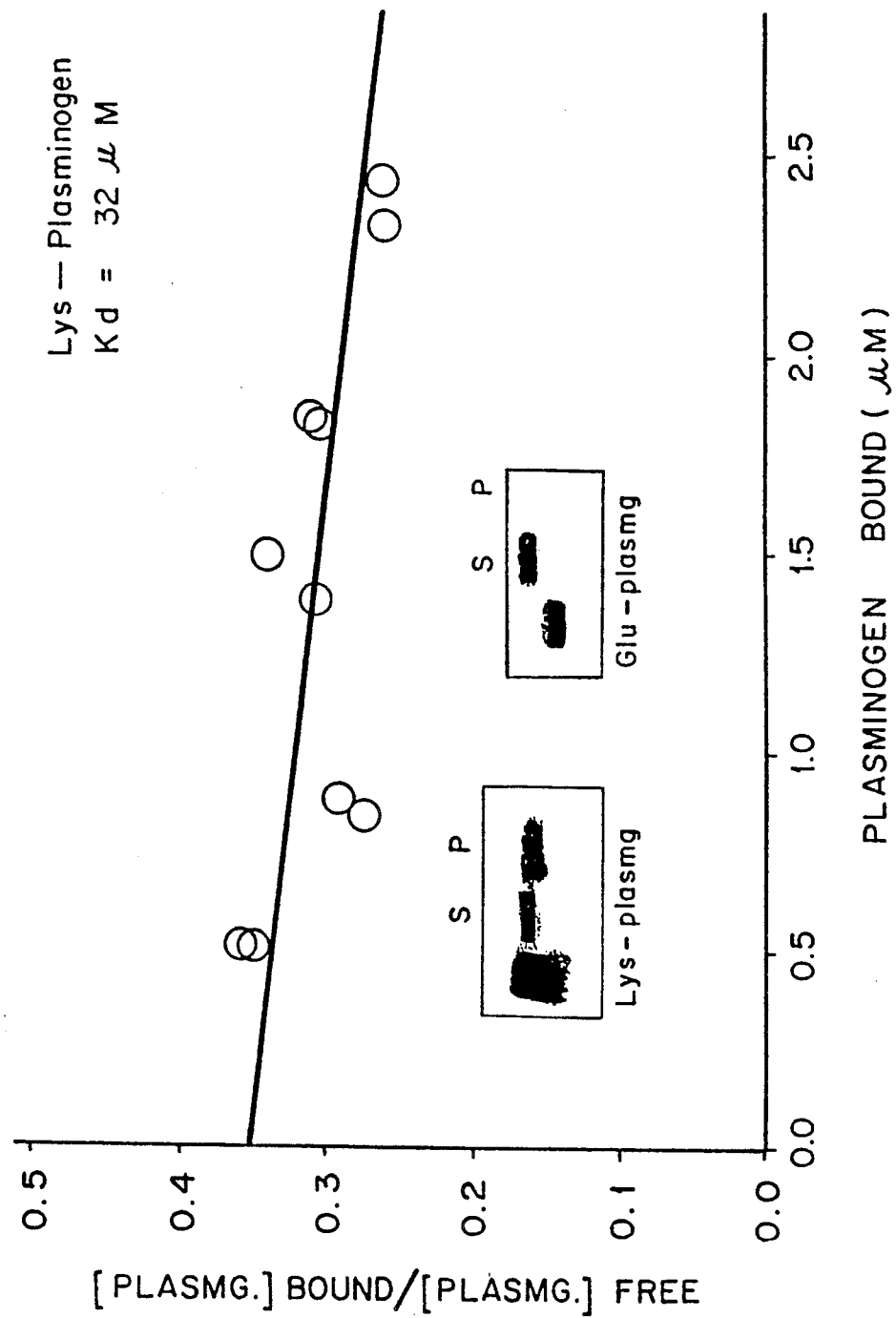

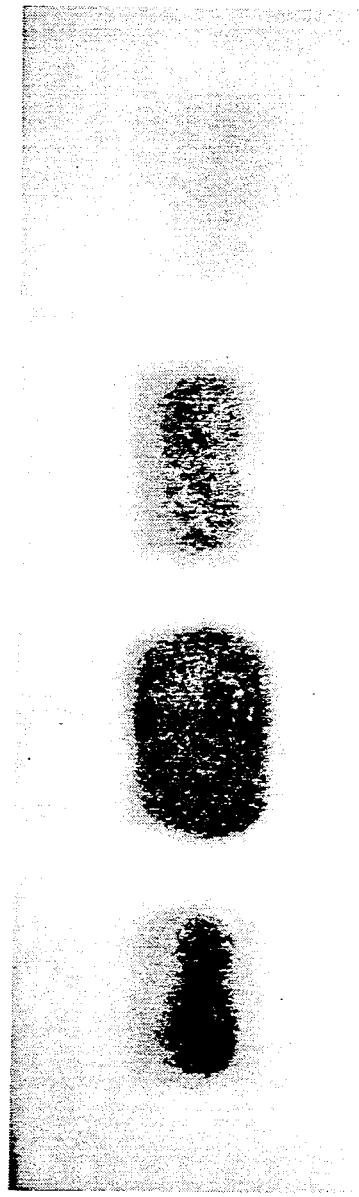

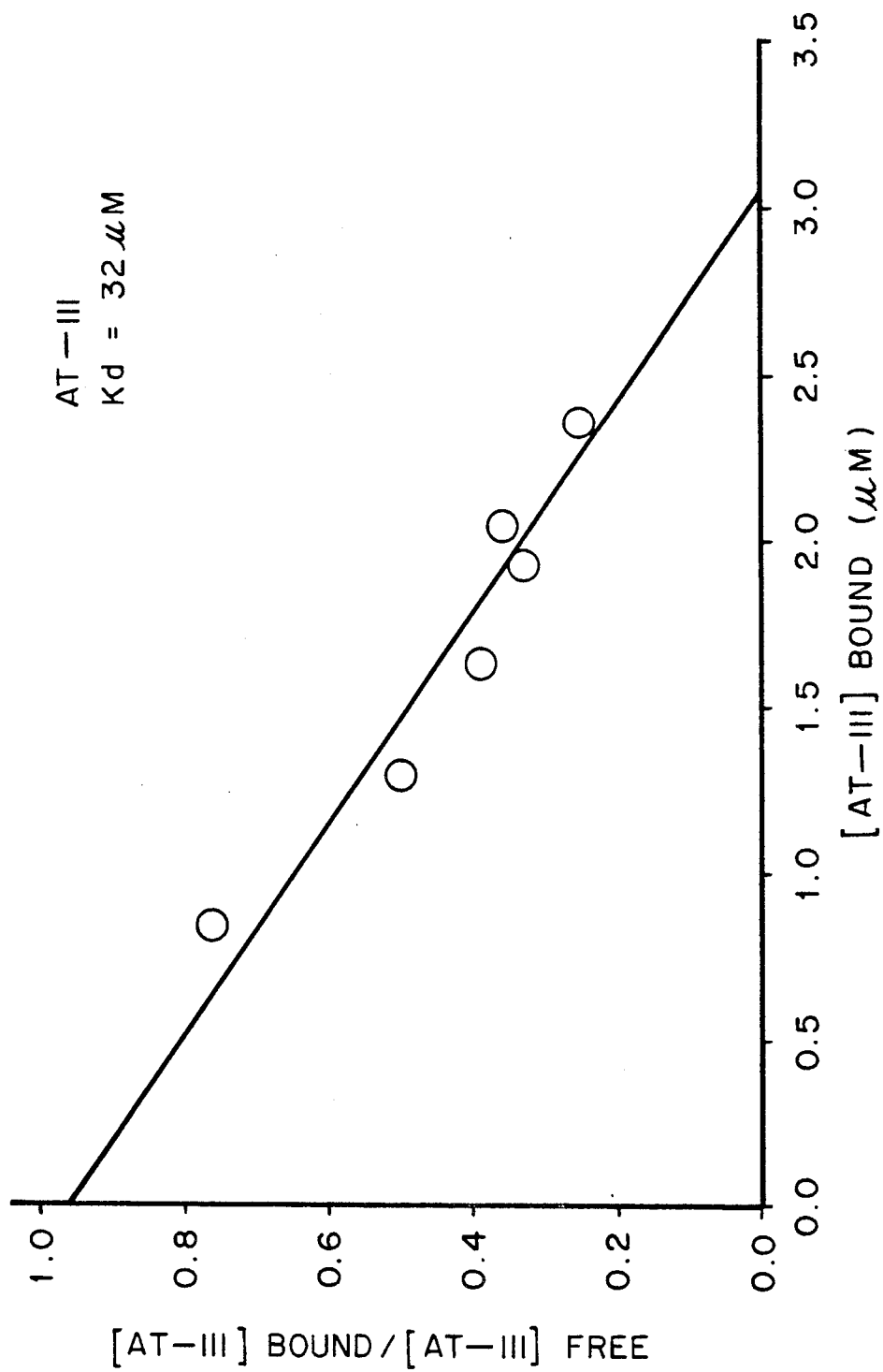

PLASMINOGEN ACTIVATION BY t-PA IN THE PRESENCE OF HEPARIN FRACTIONATED ON A rt PA-SEPHAROSE COLUMN

USE OF A LOW AFFINITY-HEPARIN FRACTION IN CONJUNCTION WITH T-PA FOR THROMBOLYTIC THERAPY

BACKGROUND OF THE INVENTION

1. Field Of The Invention

This invention relates to the use of t-PA and a heparin fraction which has low affinity for t-PA in a composition for thrombolytic therapy.

2. Background Of The Related Art

Pathologies of blood coagulation such as heart attacks, strokes, and the like, account for approximately fifty percent (50%) of all hospital deaths. These diseases are caused by the development of thromboses, or blood clots, at inappropriate locations within the cardiovascular system. Blood clot formation derives from a series of events, called the thrombolytic cascade, in which the final steps involve the formation of the enzyme thrombin. Thrombin converts circulating fibrinogen protein into fibrin, a mesh-like structure which forms the blood clot. The thrombolytic cascade is highly regulated, it can be suppressed by heparin, which inhibits the coagulation of blood. See FIG. 1, Scheme I. shows the Thrombolytic Cascade, the clot formation process in which thrombin joins with circulating fibrinogen in the blood stream to form fibrin, the mesh-like structure which makes up the clot. Scheme II shows the fibrinolytic, i.e. the clot dissolution mechanism of the Thrombolytic Cascade.

The life-saving process of clot production in response to an injury can become life-threatening when it occurs at inappropriate places in the body. For example, a clot can obstruct a blood vessel and stop the supply of blood to an organ or other body part. Equally life-threatening are clots that become detached from their original sites and flow through the circulatory system causing blockages at remote sites, these clots are called embolisms.

The Thrombolytic Cascade involves a series of transformations due to a succession of the zymogen activations. In the Thrombolytic Cascade, the activated form of one enzyme factor initiates the activation of the next enzyme. The numerous steps of the Cascade yield a large amplification factor to assure a rapid response to trauma or injury. Clotting, therefore, involves the interplay of two systems: the intrinsic pathway which can be triggered by contact with charged surfaces, e.g. glass, and the extrinsic pathway which is triggered by trauma to the tissue. These two systems converge to a final common pathway that results in the production of the fibrin clot, a transformation mediated by thrombin, a proteolytic enzyme. Thrombin is responsible for the conversion of the highly soluble fibrinogen, into insoluble fibrin.

The conversion of fibrinogen to fibrin can be inhibited by a plasma protease inhibitor called Antithrombin III ("AT III"). AT-III is a relatively slow inhibitor of thrombin, although in the presence of heparin, the rate of inhibition of thrombin by AT-III is considerably enhanced Thus, heparin is a very powerful blood clotting inhibitor.

The clot, however, once formed, can eventually be dissolved by a group of enzymes of the fibrinolytic system. A major component of the fibrinolytic system is a plasma protein called plasminogen which can be converted in the blood to plasmin. Formation of plasmin is mediated by other enzymes called plasminogen activators.

Plasminogen activators ("PA's") are serine proteases which convert the proenzyme plasminogen into plasmin, an enzyme with a broad substrate specificity. When circulating freely in the blood, plasmin degrades several proteins, including fibrinogen and some coagulation factors. Two distinct types of PA's are known; urokinase plasminogen activator ("u-PA") and tissue-type plasminogen activator ("t-PA"). Both u-PA and t-PA are currently being used as thrombolytic agents, see for example, Verstraete, et al., Blood, 67, 1529 (1986); t-PA is widely preferred over u-PA, since t-PA's activity is strongly stimulated by the presence of fibrin, the main component of blood clots. See, Hoylaerts et al., *J. Biol. Chem.*, 257, 2912 (1982). Thus, intravenously injected t-PA could induce a limited systematic lysis of fibrinogen and other substrates with the majority of its plasmin-generating activity confined to the areas of fibrin clots.

Four major clinical trials have examined the effectiveness of t-PA for thrombolysis in myocardial infarction; see, Collen et al., Circulation, 70, 1012 (1984); The TIMI Study Group, New England Journal of Medicine, 312, 932 (1985); Verstraete M. et al., Lancet, 1, 842 (1985); and Verstraete, M. et al., Lancet, 2, 965 (1985). In these trials, streptokinase, a non-enzyme protein produced by strains of $\beta$-hemolytic streptocci, was also tested for its properties as an indirect activator of the fibrinolytic system. These trials have shown that the frequency of bleeding complications was not significantly different for all agents tested. Also, systemic fibrinogenolysis was still apparent in t-PA treated patients, although it was less pronounced than with either streptokinase or u-PA.

Heparin also interacts with the fibrinolytic system. The interaction of heparin with t-PA in the fibrinolytic system results in an increase in the stimulation by t-PA of the conversion of plasminogen to plasmin. In addition, heparin binds to t-PA and decreases the stimulatory effect of fibrin on the action of t-PA.

The ability to specifically dissolve abnormal blood clots has long been a profoundly important clinical goal. The study of the intricate system of physiological thrombolysis and fibrinolysis (the dissolution of fibrin) has been a rapidly growing field which has resulted in the development of a new generation of thrombolytic agents.

Previous therapeutic treatments for dissolving life-threatening clots have included injecting into the blood system various enzymes which are known to break down fibrin. The problem with these treatments is that the enzymes were not site specific, and therefore, would do more than just cause dissolution of the clot. In addition, these enzymes interfere with and destroy many vital protein interactions that serve to keep the body from excessively bleeding due to the many minor injuries it receives on a daily basis. Destruction of these safeguards by these enzymes can lead to serious hemorrhaging and other potential fatal complications. See FIG. 1, Scheme II.

Recently, t-PA has shown promise as a thrombolytic agent. Because the activity of t-PA must be stimulated by the presence of fibrin, injected t-PA normally has little activity in the mammalian, such as human, circulatory system. In the vicinity of a clot, however, the presence of fibrin stimulates t-PA activity which then stimulates the conversion of plasminogen to plasmin to degrade the clot.

Even though t-PA occurs naturally in the mammalian (e.g. human) circulatory system, it is difficult to isolate, and until recently, naturally occurring t-PA has only been available for therapeutic use in very small quantities. Recent advances in genetic engineering have made it possible to produce large amounts of recombinant t-PA ("rt-PA") for research and clinical use. See U.S. Pat. Nos. 4,752,603; 4,751,084; and 4,753,879, the entire disclosures of which are incorporated by reference herein The large scale production and use of t-PA alone, however, has not solved all of the problems endemic to clotting disorders. One severe problem with the use of t-PA in clinical trials of human patients has been the rapid reformation of the clot after it has been dissolved. This clot reformation, called reocclusion, usually occurs within minutes of the clot being dissolved To prevent reocclusion, heparin, which inhibits blood coagulation, has been given in conjunction with t-PA therapy, Heparin is a complex glycosaminoglycan, illustrated in FIG. 2, isolated from a variety of natural sources. Usually, heparin is injected prior to, during, and after treatment with t-PA. Heparin is a valuable anticoagulant which acts catalytically to disrupt the action of thrombin. Previous publications have indicated that heparin can induce fibrinolysis in vivo and in vitro; see for example, Vinazzer et al., *Influence of Heparin; of Different Heparin Fractions and of a Low Molecular Weight Heparin-Like Substance on the Mechanisms of Fibrinolysis*, Throm. Res., 27, 341 (1982); however, the mechanisms of interaction of heparin in the thrombolytic cascade have remained obscure. The combination of t-PA and heparin seem to be the key to effectively dissolving blood clots and preventing their reocclusion in heart attack victims.

An article by Turpie et al., *A Randomized Controlled Trial of a Low-Molecular-Weight Heparin (Enoxaparin) to Prevent Deep-Vein Thrombosis in Patients Elective Hip Surgery*, New England Journal of Medicine, 315, 925-929 (1986), attributes the reduced hemorrhagic effects of a low molecular weight heparin fraction to lower inhibition of platelet function by the low molecular weight heparin fraction than by standard heparin, and a higher antithrombotic activity observed in these experiments was attributed to higher levels of the low molecular weight heparin. Turpie et al. conclude it is unlikely that the low molecular weight heparin fraction is inherently more antithrombotic than standard heparin.

The previously mentioned article by Vinazzer, et al., discloses that the magnitude of fibrinolysis depends on the degree of sulfation in heparin fractions since a low molecular weight heparin fraction with a high number of sulfate bonds was considerably more active in fibrinolysis than a low molecular weight fraction of standard heparin. An editorial by Sherry, *Tissue Plasminogen Activator* (t-PA) *Will It Fulfill Its Promise?*, in the New England Journal of Medicine, Vol 13, No. 16, 1014-1017 (1985), discusses the problems of bleeding complications resulting from recombinant t-PA therapy in conjunction with simultaneous heparin therapy to prevent rethrombosis, but does not suggest any manner of solving those problems.

An article by deProst, *Heparin Fractions and Analogues: A New Therapeutic Possibility For Thrombosis*, Trends in Pharmacological Sciences, 7, 496-500 (Dec.

1986), discloses reduced interaction with platelets by low molecular weight heparin fractions and natural or semi-synthetic heparin analogues and the longer duration of action in vivo of these compounds compared to heparin. The article suggests investigation into the mechanisms of action of these fractions and analogues of heparin to define their indications in treatment of thrombosis, but does not disclose how these investigations may be carried out.

Paques et al., *Study on the Mechanism of Action of Heparin and Related Substances on the Fibrinolytic System: Relationship Between Plasminogen Activators and Heparin*, Thrombosis Research 42, 797-807 (1986) discloses that t-PA and u-PA bind tightly to heparin-SEPHAROSE, and that the plasminogenolytic and the fibrinogenolytic activity of t-PA and u-PA can be stimulated at low unfractionated heparin concentrations.

A human pharmacological study comparing conventional heparin and a low molecular weight heparin fragment was reported by Bratt et al., in Thromb. Haemostasis, 53, 208-211 (1985).

Previous results by the inventors, herein, Andrade-Gordon, P., and Strickland, S., were reported in *Interaction of Heparin with Plasminogen Activators and Plasminogen: Effects on the Activation of Plasminogen*, Biochemistry, 25, 4033 (1986), and have shown that heparin interacts with t-PA, thus, interfering with t-PA's site specific action.

One problem with the use of heparin with t-PA is that the activity of t-PA which, in addition to being stimulated by fibrin, as previously noted, is also stimulated by heparin. Accordingly, the concomitant injection of heparin and t-PA in the mammalian circulatory system has two potentially deleterious consequences. First, heparin could activate t-PA in the general circulatory system, causing destruction of blood components with resulting hemorrhaging Second, heparin inhibits the binding of t-PA to fibrin and could prevent the localization of the enzyme at the site of the clot. See, FIG. 1, Scheme 2. The cumulative affect of both of these actions would reduce the specific fibrin-(clot)-dependent activity of t-PA and increase the non-specific protein degradation, both of which are therapeutically undesirable.

In their aforementioned article, the inventors herein primarily describe the activation of plasminogen by unfractionated heparin and set forth their theory to explain the interaction between heparin, t-PA and u-PA in plasminogen activation In addition, in that article, two fractions of heparin separated on the basis of their affinity for antithrombin-III-SEPHAROSE differed greatly in their ability to stimulate AT-III activity, although not differing in their enhancement of t-PA mediated plasmin activity.

More recently, the inventors herein have provided an overview of their work in *New Strides in Immediate Treatment for Heart Attacks*, Biotechnology Network, a newsletter of the State University of New York at Stony Brook (May/June 1987). In this article, the inventors herein speculate that it might be possible to fractionate heparin and separate the components responsible for anticoagulation activity from those components that activate t-PA. The inventors also propose the possibility of using recombinant DNA techniques to produce a t-PA enzyme which may be effective in clot dissolution but would not interact with heparin. No suggestion is made, however, of how to achieve these goals. Nor is there any discussion of using these modified components in combination therapy.

The aforementioned articles explore the action of heparin, its various components and analogues, but none describes a heparin fraction which can be safely used in conjunction with t-PA to prevent reocclusion without unwanted stimulation of, or interference with t-PA activity.

Accordingly, it is an object of the present invention to provide an effective thrombolytic therapy for treating mammals, including humans without reducing specific fibrin- o dependent activity and without increasing non-specific protein degradation.

It is a further object of this invention to provide a heparin fraction and a method for its isolation which, in conjunction with t-PA therapy in mammalian, including human patients is effective in preventing reocclusion without causing uncontrolled bleeding by stimulating or interfering with t-PA activity.

It is also an object of the present invention to provide a therapeutic composition which is site specific.

Another object of the present invention is to provide a therapeutic composition which prevents reocclusion of the clot.

It is yet another object of the present invention to provide a new composition for thrombolytic therapy which does not inhibit the binding of t-PA to fibrin, so that t-PA can localize at the site of the clot.

Still another object of the present invention is to provide a new composition for thrombolytic therapy which can inhibit thrombosis without accelerating t-PA activity in the general circulation causing destruction of blood components and resulting in hemorrhage.

Furthermore, it is an object of the present invention to provide a method of thrombolytic therapy with which reocclusion does not occur and without interference with t-PA and fibrinogen function.

SUMMARY OF THE INVENTION

The present invention provides a method for thrombolytic therapy which includes administering to a mammalian, e.g., human, heart attack victim an effective amount of tissue-type plasminogen activator (t-PA), and a heparin fraction having low affinity for t-PA ("LA-heparin") in an amount which, in conjunction with the t-PA, prevents reocclusion. Accordingly, when the method for thrombolytic therapy of the present invention is used, the t-PA dissolves blood clots while the LA-heparin prevents reocclusion without the side effects of unfractionated heparin, including uncontrolled bleeding due to stimulation of fibrinolytic activity.

The present invention also includes a method for isolating and preparing and standardizing the LA-heparin fraction.

In the present invention, the LA-heparin does not significantly stimulate the activation of plasminogen by t-PA with or without the presence of fibrinogen fragments. Therefore, there is no interference with the function of t-PA in the fibrinolytic process.

For a better understanding of the present invention, reference is made to the following description and the accompanying drawings, the scope of which is defined by the claims.

BRIEF DESCRIPTION OF THE DRAWINGS

FIG. 2 illustrates the molecular structure of unfractionated heparin.

FIG. 4 is a graph showing the effect of NaCl on the activity of a mixture of t-PA, and Lys-plasminogen, as described in Example 2C.

FIG. 5 is a graph comparing the initial rates of hydrolysis of HMW-heparin, as described in Example 3A and LMW-heparin, as described in Example 3B, respectively, illustrating the effect of the respective heparin fraction on fibrin stimulation of t-PA activity.

FIG. 7 is a graph showing the effects of HMW-heparin and LMW-heparin on the inactivation of thrombin by AT-III, as described in Example 5.

FIG. 10a is a graph plotting ul of settled LMW-heparin-SEPHAROSE gel vs. absorbance at 631 nm, as described in Example 6c in order to determine the amount of LMW-heparin covalently coupled to the SEPHAROSE. FIG. 10b is a standard curve prepared by plotting the absorbance at 631 nm of known amounts of LMW-heparin, as described in Example 6c, in order to determine the values for FIG. 10a.

FIG. 11a is a Scatchard Plot which shows the binding of Lys-plasminogen to LMW-heparin-SEPHAROSE, as described in Example 6C. The insert shows the results of SDS-PAGE analysis of Lys-plasminogen and Glu-plasminogen bound in the pellet (P) and unbound Lys and Glu-Plasminogen in the supernatant (S). FIG. 11b is a comparison of electrophoreses showing the binding of t-PA to HMW-heparin-SEPHAROSE and the binding of t-PA to LMW-heparin-SEPHAROSE, as described in Example 6C. FIG. 11d is a Scatchard plot showing LMW-heparin binding to AT-III.

DETAILED DESCRIPTION OF THE INVENTION

Figure 1:
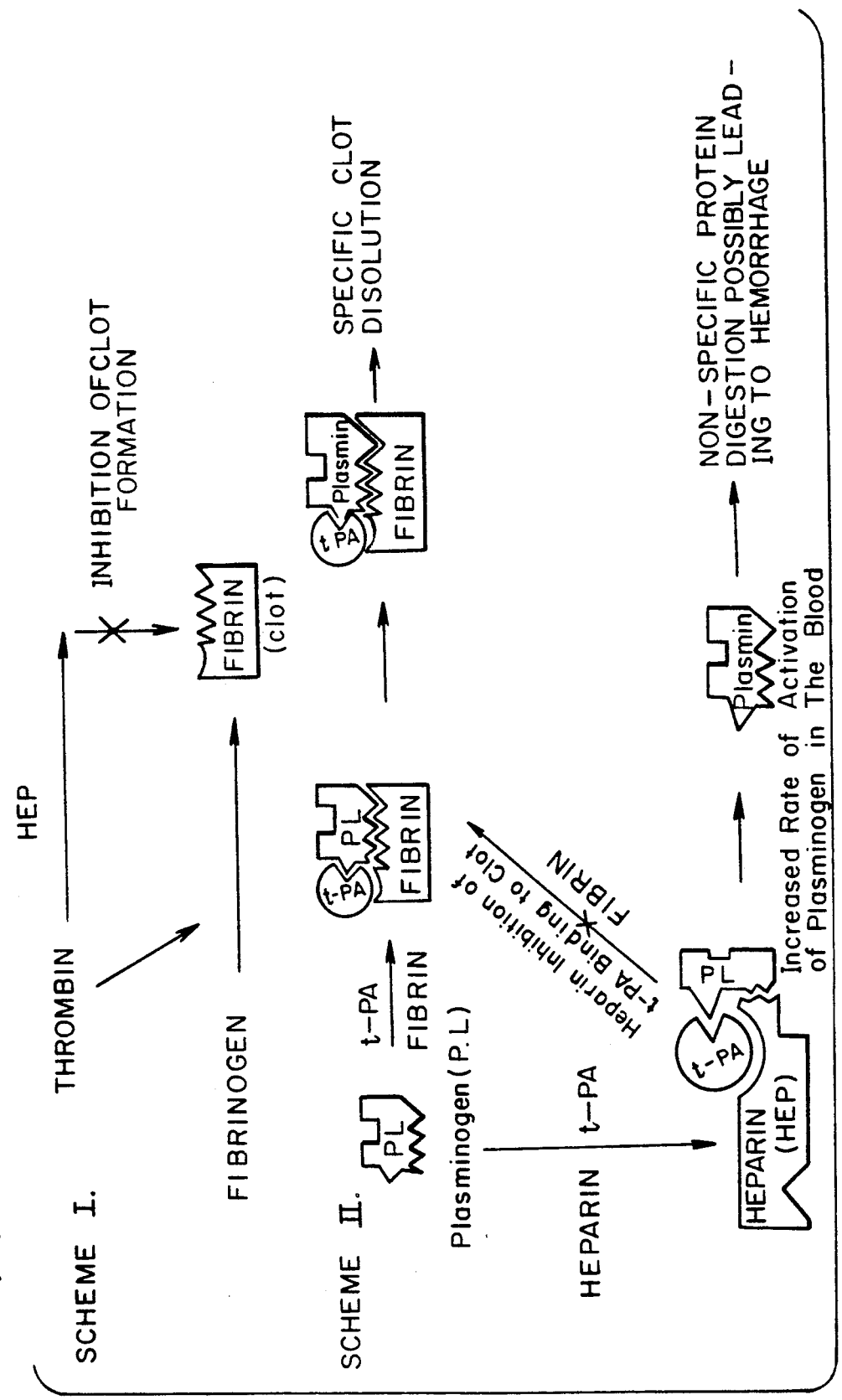
FIG. 1 is a schematic representation of the thrombolytic cascade. Scheme I shows the interactions present in clot formation, in which thrombin joins with circulating fibrinogen to form fibrin, and also shows the inhibitory effect of heparin. Scheme II shows the fibrinolytic, clot dissolution system.

The activity of tissue plasminogen activator (t-PA) and urokinase-type plasminogen activator (u-PA) is stimulated by heparin at concentrations reached during thrombolytic therapy. Heparin binds tightly to t-PA, u-PA, and plasminogen, and in fact decreases the usual stimulatory effect of fibrin on t-PA activity. The presence of heparin, therefore, results in a higher than anticipated level of fibrin-independent plasminogen activation by t-PA.

We have found that certain heparin fractions designated low affinity heparin (LA-heparin) differ in their interactions with the fibrinolytic system from those observed for HMW-heparin. Binding data shows that these LA-heparin fractions do not bind t-PA and Glu-plasminogen, and bind only very weakly to Lys-plasminogen. LA-heparin preparations do not stimulate plasmin formation by t-PA, however, these heparin preparations still efficiently accelerate the inhibition of thrombin by anti-thrombin III (AT-III). The results shown in the following examples illustrate that it is possible to selectively remove the fibrinolytic stimulating properties of heparin while leaving the classical anticoagulant characteristics intact.

Initially, we used a commercially available low molecular weight heparin fraction (LMW-heparin) isolated after nitrous acid depolymerization of HMW-heparin as described in Example 1. During the course of our investigations in performing the experiments described in Examples 2–6, we realized that a therapeutically more active fraction may be obtained by separating HMW-heparin on the basis of its affinity to t-PA, and selecting those heparin fractions having a low affinity for t-PA. Those LA-heparin fractions would be more effective than the LMW-heparin fractions which were obtained by nitrous acid depolymerization.

Even though the LMW-heparin fractions show very little interaction with t-PA and u-PA, the preparation of these fractions by nitrous acid depolymerization of HMW-heparin molecules is disadvantageous because it relies on a random cleavage process, resulting in a mixture of different low molecular weight fragments. Each fragment, however, may have different properties and activities. To date, heparin units have not been completely standardized, as commercially available heparin fractions vary due to the depolymerization process. Accordingly, investigators have been using a number of different low molecular heparin fractions for various purposes, however, due to the heterogeneity of the heparin fractions, per se, none of these fractions could reliably be defined and standardized. By contrast, the preparation of the LA-heparin fraction separated on the basis of its affinity towards t-PA (or, similarly based on its affinity to u-PA and plasminogen if desired) results in a much more homogeneous sample. Therefore, not only are the LA-heparin fractions more effective than the LMW-heparin fractions, these fractions now can be standardized based on their affinity to t-PA, u-PA and their thrombolytic activity.

Accordingly, in preparing LA-heparin, t-PA was first bound to heparin-SEPHAROSE and HMW-heparin was eluted through the t-PA-SEPHAROSE column to isolate a low affinity heparin fraction The specific methodology for isolating this LA-heparin fraction is described in Example 7, and the properties of this LA-heparin fraction are described in Examples 8–10. Our experiments have shown that the LA-heparin fraction retains its anti-coagulant activity but that does not enhance plasminogen activation by t-PA. Therefore, thrombolytic therapy using LA-heparin in conjunction with t-PA should reduce the dangers of hemorrhaging associated with thrombolytic therapy of heart attack victims.

Presently, unfractionated HMW-heparin is being administered to heart attack patients according to the following dosage protocol:

HMW-heparin is injected intravenously at a concentration of about 5,000 Units, as a bolus at coronary angiography. Three hours after the initial bolus, a constant dosage of 1,000 Units per hour HMW-heparin is again introduced intravenously. The HMW-heparin dosage is adjusted to maintain the activated partial thromboplastin time ("APTT") at about 1.5, which is approximately two times the normal APTT, until predischarged catherization is performed eight to ten days later.

Approximately 100 mg of t-PA is introduced over the three-hour period following a coronary angiograph. About 60 mg is given in the first hour, with about 6–10 mg as an initial bolus over approximately a 1–2 minute period, and the remaining dosage infused slowly over the remainder of the first hour. Approximately another 40 mg of t-PA is infused slowly over the remaining two hours, at a dosage of about 20 mg per hour.

We believe that the LA-heparin dosage should be adjusted below the corresponding HMW-heparin dosage due to the long biological half-life of LA-heparin. We believe that the use of a single daily injection of approximately 7,500 anti-Xa units of LA-heparin will be more effective in preventing thrombosis than about 5,000 anti Xa units of HMW-heparin repeated twice daily (every twelve hours). We also believe that the dosage of t-PA should remain the same or preferably reduced from the dosage described above.

The treatment protocol for heart attack patients is provided strictly for the purpose of illustrating one known treatment protocol. This protocol is what we presently believe is the preferred method of treating heart attack patients with t-PA-heparin following coronary angiography. The specific dosage and timing is not intended to describe the only known procedure for this treatment, but to merely illustrate one example of such protocol. Those skilled in the art will appreciate that these dosages can be varied, and that under different conditions, the timing and quantity of the dosages would vary accordingly.

Likewise, the recommended dosages for the LA-heparin fractions are intended to provide what we believe would be a clinically acceptable treatment, however, those of ordinary skill in the art may adjust these dosages to comply with the specific clotting conditions being treated. In addition, in some instances, it may be preferred to administer the LA-heparin and t-PA as one bolus, or that due to the lack of interaction between the LA-heparin and t-PA, the dosage of t-PA may be decreased.

In addition, u-PA and plasminogen may be substituted for t-PA and used with LA-heparin fractionated either on the basis of its affinity t-PA, to u-PA or plasminogen.

EXAMPLE 1

Identification and Preparation of a LMW-Heparin Fraction

A low molecular weight-heparin (LMW-heparin) fraction is commercially available from the Sigma Chemical Company, St. Louis, Mo. ("Sigma"), Catalog No. H5640, Lot No. 106F-0105. The fraction is prepared from fractionated HMW-heparin derived from porcine intestinal mucosa. The sodium salt of the LMW-heparin fraction is obtained by nitrous acid depolymerization of the HMW-heparin and selection of the fraction having an average molecular weight in the range of 3,000–8,000 daltons, preferably 4,000 to 6,000 daltons, an Anti-Xa activity >150 U/mg, and an activated partial thrombin time (APTT) >40 IU/mg as defined by Sigma 1987 Catalog No. H5640.

EXAMPLE 2

Comparison of the Effects of LMW-heparin on the Activation of Plasminogen by t-PA The HMW-heparin and the LMW-heparin fractions described in Example 1 were tested in the presence of t-PA for their ability to stimulate the conversion of plasminogen to plasmin. The assay defects lysis of the amide bond of plasminogen in determining their "amidolytic plasmin activity."

Amidolytic Assay Procedure:

2A. The ability of unfractionated HMW-heparin to stimulate amidolytic plasmin activity of a mixture of Lys-plasminogen or Glu-plasminogen and t-PA was measured according to the protocol, previously published by the inventors herein in Biochemistry, 25, 4033 (1986) (hereinafter "the Biochemistry Paper").

Unfractionated HMW-heparin derived from porcine intestinal mucosa, molecular weight 20,000, was obtained from Sigma. The structure of HMW-heparin is shown in FIG. 2. Both the calcium ("Ca") and the sodium ("Na") salts of heparin were tested. The Ca-heparin salt, obtained from the Sigma in a concentration of 148 units/mg, and the Na-heparin salt, also obtained from Sigma in a concentration of 153 units/mg.

To a buffered solution of 200 ul of 0.1M Tris-HCl, pH 8.1, 0.1% (V/V) Tween 80, 0.3 mM chromogenic plasmin substrate H-D-Val-Leu-Lys-pNA (S-2251, Kabi, Sweden) was added. To this mixture, HMW-heparin fractions (the Ca and Na salts, respectively) in concentrations ranging from 0 to 25 units/ml and 0.42 $\mu$M Glu- or Lys- plasminogen were added.

The Glu-plasminogen was prepared from human plasma by chromatography with L-lysine-SEPHAROSE according to the method described by Deutsch et al., in Science, 170 1095–1096 (1970). Human Lys-plasminogen was obtained from American Diagnostics, Greenwich, Connecticut. Both forms of plasminogen appeared to be homogeneous, yielding a characteristic doublet on SDS gel electrophoresis.

To each of the foregoing solutions with varying HMW-heparin concentrations, 0.09 nM t-PA was added. The t-PA purified from human melanoma (Bowes) cell culture (476,000 international t-PA units/mg) was donated by Dr. Keith Marotti, Upjohn Co., Kalamazoo, Mich.

Figure 3A:
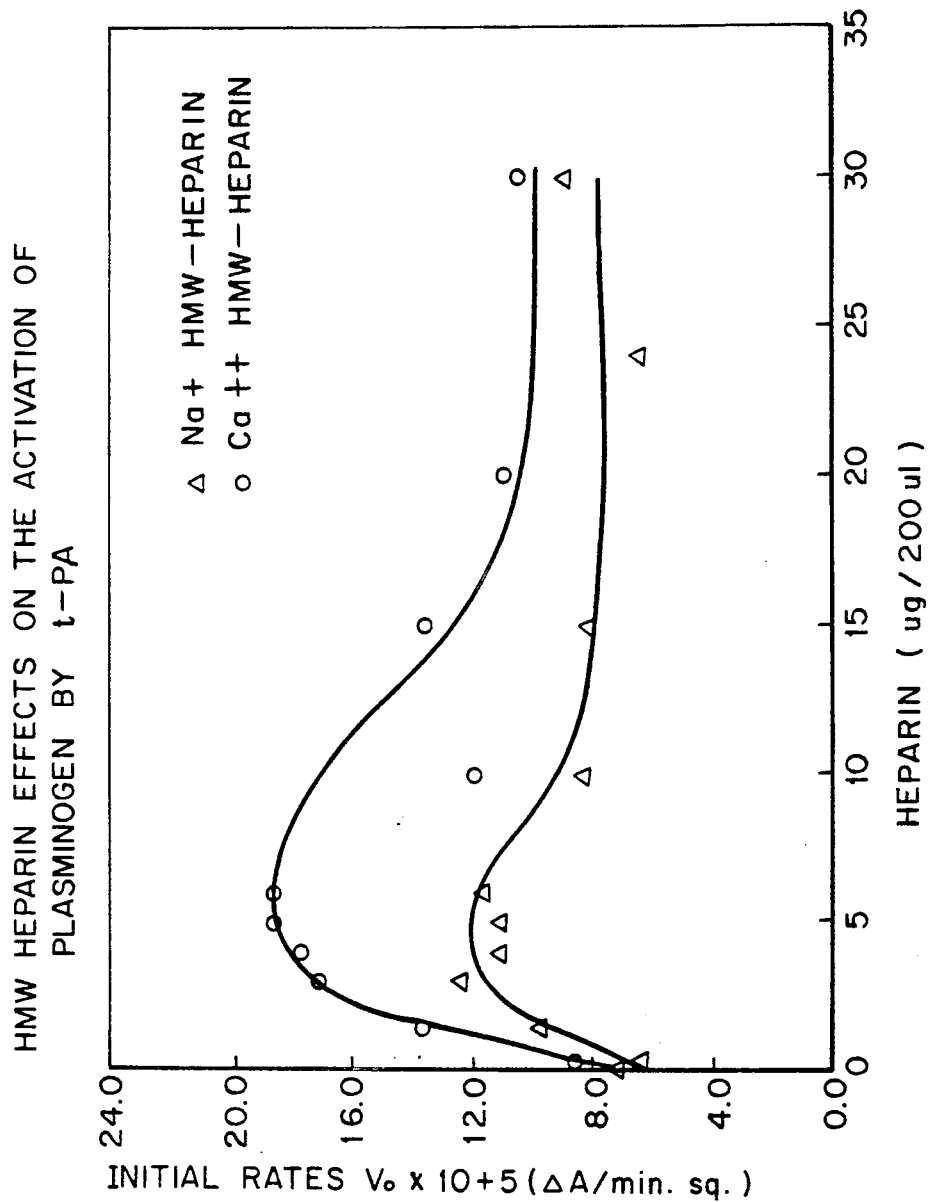
FIG. 3a is a graph showing the effect of unfractionated heparin ("HMW-heparin"), both as sodium and calcium salts on the activation of plasminogen by t-PA, prepared as described in Example 2A.

The solutions were incubated in microliter plates at 25° C. The change in absorbance ($\Delta A$) at 405 nm was measured against blanks without t-PA in a Bio-Tek model EL-308 microplate reader. The results are shown in FIG. 3a. In FIG. 3a, the initial rate of plasmin generation is plotted against the HMW-heparin sodium and calcium salt concentrations.

It should be noted that plasmin activity was actually being measured in this assay and that the plasmin concentration was increasing as a function of time due to the action of the plasminogen activators on plasminogen. Thus, plots of absorbance vs. time are parabolic, whereas plots of absorbance vs. time squared are linear. Therefore, the slopes of plots of absorbance vs. time squared were used as a measure of the rate ($V_O$) of plasmin generation. The rate of plasmin generation is the same as the rate of hydrolysis of the amide bond of plasminogen, referred to as "amidolytic plasmin activity". (For a more detailed discussion of the derivation of these calculations, see the Biochemistry Paper, at the Appendix on p.4039).

In FIG. 3a, the initial rates of hydrolysis (plasmin generation) are plotted against HMW-heparin concentrations.

Initial rates of hydrolysis were obtained by measuring the change in absorbance at 405 nm as a function of time, as described above. FIG. 3a shows that the generation of plasmin from plasminogen in t-PA-plasminogen mixtures is enhanced by the presence of HMW-heparin.

2B. LMW-heparin prepared as described in Example 1 was tested for amidolytic activity in the same manner as described for the HMW-heparin of Example 2A. In addition, LMW-heparin was tested in the presence of u-PA for its ability to stimulate amidolytic plasmin activity.

Figure 3B:
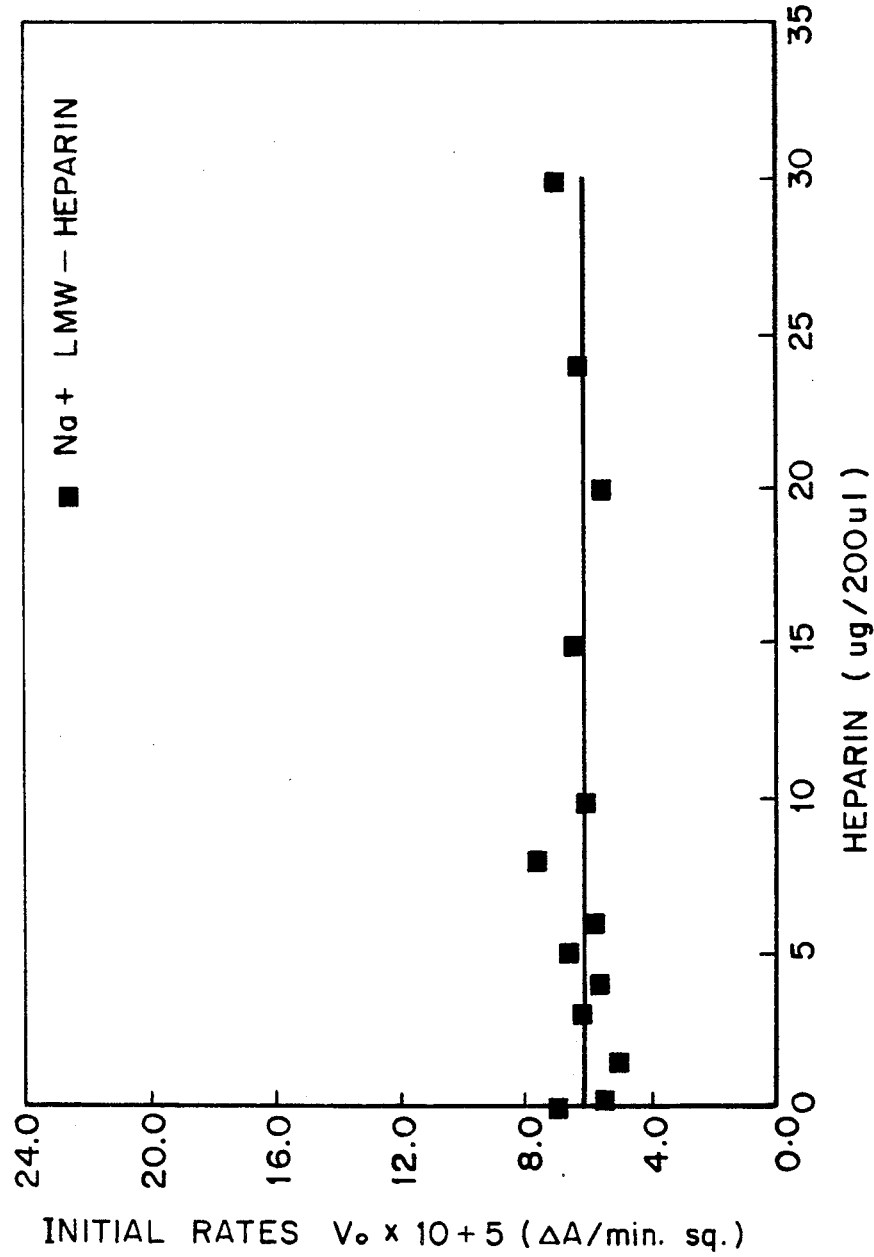
FIG. 3b is a graph showing the effect of a sodium salt of a low molecular weight heparin fraction ("LMW-heparin") on the activation of plasminogen by t-PA, as described in Example 2B.

The various concentrations of LMW-heparin tested, were prepared using a range of ratios of weights to volume of 0 to 30 μg LMW-heparin/200 μl of assay volume. The mean molecular weight for the LMW-heparin fraction was 4000-6000 daltons which is approximately ¼ of the molecular weight of the unfractionated preparation used in Example 2A (20,000 MW). Therefore, the amount of LMW-heparin used per assay, measured in μ moles of heparin/μl of assay volume, was approximately 4 times higher than the corresponding amount of the HMW-heparin in order to maintain the same molar concentration of sugar monomer per given mass of heparin. The results of this experiment, displayed in FIG. 3b, showed little or no stimulation of the amidolytic plasmin activity generated from Lys-plasminogen by t-PA in the presence of LMW-heparin. In FIG. 3b, the initial rate of plasmin generation is plotted against the concentration of the sodium salt of LMW-heparin.

Figure 3C:
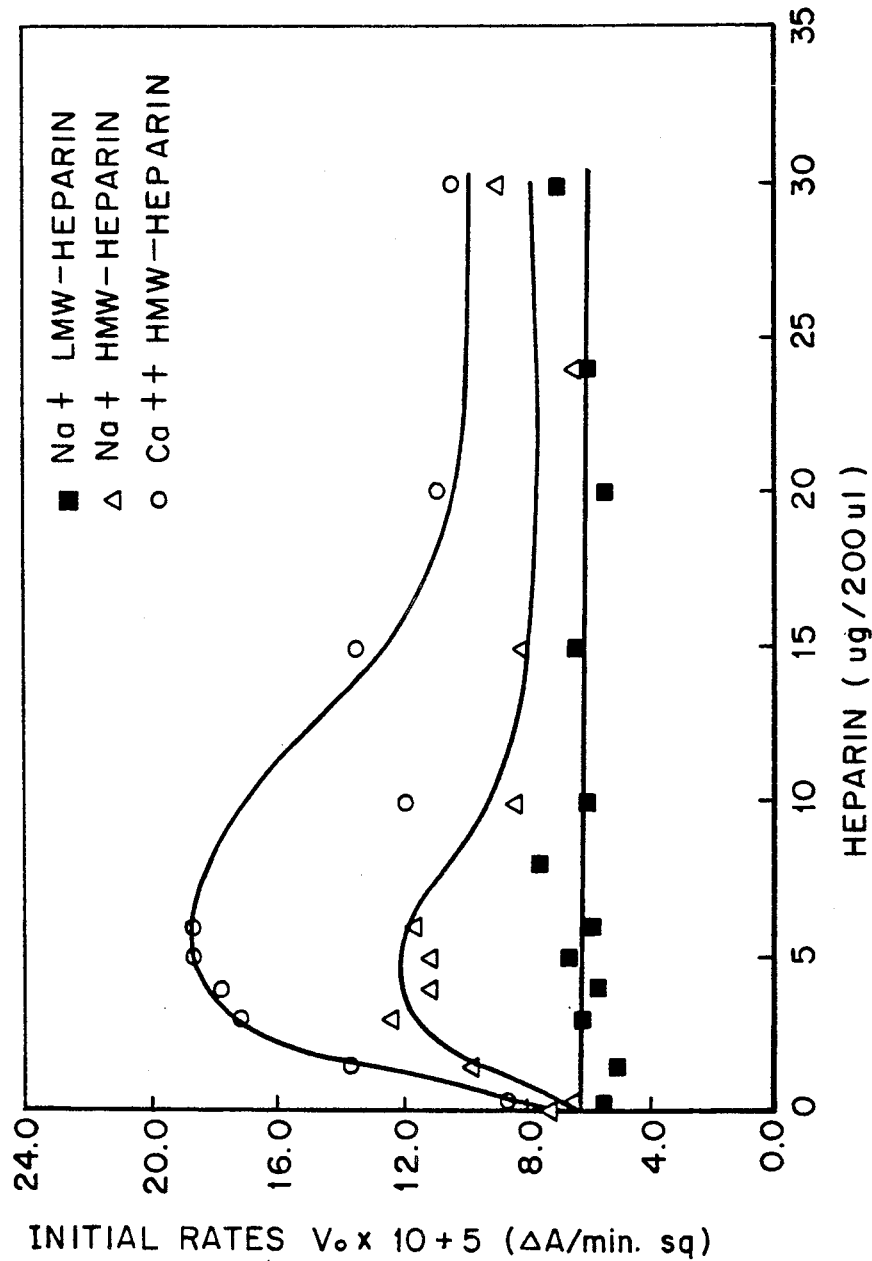
FIG. 3c is a graph showing the plotted amidolytic activity of the sodium and calcium salts of HMW-heparin superimposed on the plotted amidolytic activity of the sodium salt of LMW-heparin, as described in Example 2B.

In FIG. 3c, the results of the amidolytic activity tests for the HMW-heparin shown on FIG. 3a were superimposed onto the results for the LMW-heparin fraction shown on FIG. 3b to contrast the differences in the effect of the various heparin fractions on the activation of plasminogen by t-PA.

Figure 3D:
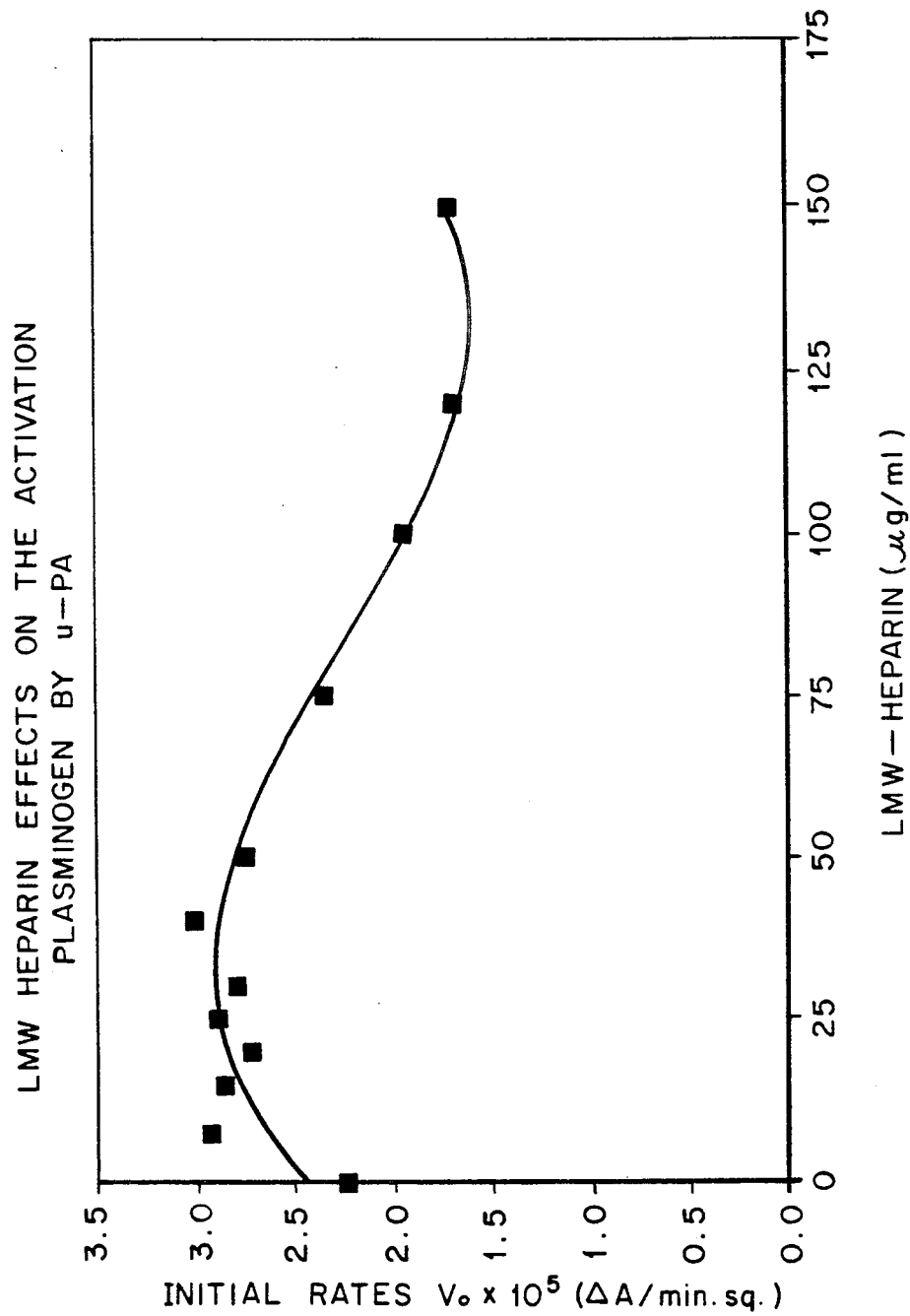
FIG. 3d is a graph showing the effect of LMW-heparin on the activation of plasminogen by u-PA, as described in Example 2B.

The results using u-PA with LMW-heparin are shown in FIG. 3d. In this case there was a slight dose-dependent stimulation of u-PA-generated plasmin activity by LMW-heparin. The magnitude of this stimulation was about 1.3-fold over control values at a dose of 25 μg/ml of LMW-heparin. At doses greater than 75 μg/ml there was a marked inhibition of plasminogen activation. In contrast, at doses above 35 μg/ml of unfractionated HMW-heparin, t-PA was stimulated 3-fold.

2C. In Example 2B, the particular LMW-heparin fraction was the Na salt obtained after nitric acid depolymerization (see Example 1). One possible explanation for the lack of enhancement by the LMW-Heparin fraction of the amidolytic activity may be an inhibition of t-PA by Na+ ions. This inhibitory effect of plasminogen activation by some metal ions has been reported by Dano and Reich, in *Proteases and Biological Control*, 357-661, edited by Reich et al., Cold Spring Harbor Laboratory, NY (1975).

To test this possibility, the effect of NaCl on the amidolytic activity of a mixture of t-PA and Lys-plasminogen was determined as described above. The amount of NaCl used was calculated based on an overestimate of Na molecules present per molecule of LMW-heparin. The results of this experiment are shown in FIG. 4. In FIG. 4, the initial rate of plasmin generation is plotted against the concentration of NaCl. FIG. 4 indicates that over the range of NaCl concentrations, Na+ ions alone did not cause a marked decrease of the amidolytic activity. Thus, this example demonstrates that the Na+ ions do not inhibit t-PA activity, and are not the cause of the lack of plasminogen stimulatory effect observed for the LMW-heparin fraction.

EXAMPLE 3

Effect of Heparin on Fibrin Stimulation of t-PA Activity

3A. This example tested the effect of HMW-heparin on fibrin stimulation of t-PA activity. Since it has been well established that fibrin or fibrinogen fragments stimulate the activation of plasminogen by t-PA, Verheijen et al., Thromb. Res., 32, 87-92 (1983), the amidolytic plasmin activity of a t-PA-plasminogen mixture was tested by preparing the solution described in Example 2A, except that 0-3 units/ml HMW-heparin were used, and 25 μg/ml soluble fibrinogen fragments were added to the solution.

Bovine fibrinogen, 77% clottable was obtained from Sigma Chemical Co., St. Louis, Mo., and precipitated with ammonium sulfate, resuspended in 0.6M NaCl, and then precipitated twice with 77% ethanol in the presence of lysine as described by the method of Strickland et al., in J. Biol. Chem., 251, 5694-5702 (1976). The soluble fibrinogen fragments were prepared from the fibrinogen by treatment with cyanogen bromide according to the method of Verheijen et al., in Thromb. Hemostasis, 48, 266-269 (1982) at room temperature followed by dialysis against distilled water.

In FIG. 5 the initial rate of plasmin generation is plotted against heparin concentrations for both HMW- and LMW-heparin fractions. The results shown in FIG. 5 indicate that in the presence of low concentrations, i.e., less than (1 ug/ml) of HMW-heparin, fibrinogen fragment stimulation was markedly reduced. For example, fibrinogen fragment stimulation was diminished to approximately two-thirds its original value by less than 0.5 ug/ml of HMW-heparin. At higher concentrations of HMW-heparin, up to 2.5 μg/ml the activity was even more suppressed, although it increased gradually with heparin concentrations greater than 2.5 μg/ml. Thus, as shown in FIG. 3a HMW-heparin stimulated the activity of t-PA and consequently the production of plasmin in the absence of fibrinogen fragments, and as shown in FIG. 5 HMW-heparin reduced the activity of t-PA in the presence of fibrinogen. These results suggest that fibrin and HMW-heparin compete for some of the same binding sites of plasminogen and/or t-PA.

3B. The effect of LMW-heparin on fibrin stimulation of t-PA activity was tested using the same methods described in Example 3A for HMW-heparin, and the results were again plotted on FIG. 5. As shown in FIG. 5, the fibrin stimulatory activity of t-PA was reduced from $12.3 \times 10^{-5}$ Δ A/min$^2$, in the absence of LMW-heparin fraction, to $10.2 \times 10^{-5}$ Δ A/min$^2$, in the presence of 0.50 μg/ml of the LMW fraction. This is in contrast to the larger drop to $9.2 \times 10^{-5}$ Δ A/min$^2$, in the stimulatory effect of fibrinogen on t-PA observed when the same concentrations of HMW-heparin were present, as described in Example 3A. Also, by contrast to HMW-heparin, which caused a continual drop in stimulatory effect at least until a heparin concentration of 2.5 ug/ml was reached, the suppression of fibrin stimulatory activity leveled off at a concentration of only 0.4 to 0.5 μg/ml of LMW-heparin.

Accordingly, LMW-heparin apparently causes a significantly less pronounced decrease of the stimulatory effect of fibrinogen on t-PA than that observed for HMW-heparin. FIG. 5 shows, however, that there is still a small level of interference with fibrin stimulation by t-PA caused by LMW-heparin.

Accordingly, this Example shows that LMW-heparin does not significantly interfere with fibrin stimulation by t-PA and the resulting conversion of plasminogen to plasmin which leads to specific clot dissolution (see FIG. 1, scheme II). The lesser level of interference, however, suggests that some, albeit a lesser level of competition for t-PA still exists between this LMW-heparin fraction and fibrinogen.

EXAMPLE 4

Analysis of Plasminogen Activation by SDS-GEL Electrophoresis

4A. Radioiodination of Plasminogen

Human Glu- and Lys-Plasminogen described in Example 2A, were radiolabeled with iodogen, obtained from Pierce Chemical Co., Rockford, Ill., and with Na$^{125}$I obtained from New England Nuclear. The plasminogens were radiolabeled as described by Markwell, et al., in Biochemistry, 17, 4807–4817 (1978), except that spun Sephadex G-50 columns, obtained from Pharmacia, Sweden, were used to separate the protein from unreacted $^{125}$I. The iodinated proteins had specific activities between 0.3 and 0.5mCi/mg. The labeled plasminogen preparations were indistinguishable from the unlabeled proteins by SDS-PAGE or urokinase-induced activation.

4B. The effect of HMW-heparin on the t-PA mediated generation of plasmin from plasminogen was analyzed in 500 µl of a reaction mixture prepared as follows: A 30µg sample of plasminogen was mixed with of iodine radiolabeled plasminogen, 15 µg of 1.5 µM HMW-heparin and 0.04 µM t-PA. The reaction mixture was incubated in 0.1M Tris-HCl, pH 7.4, containing 50% glycerol to suppress plasmin activity, as described by Robbins et al., Methods Enzymol., 19, 184–199 (1970).

A control sample was prepared in the same manner but without the addition of HMW-heparin.

Four samples of the reaction mixture and control sample, as described above, were incubated at 25° C. for 0, 12, 24 and 36 hours, respectively, at which times the samples were diluted with 2 ml of 2% w/v SDS and 20 mM DTT, adjusted to 10% TCA and cold centrifuged. The pellets were dissolved in the SDS/DTT buffer described above, and applied to SDS-8% polyacrylamide slab gels according to the method of Laemmli, in Nature (London), 227, 680–685 (1970).

Figure 6A:
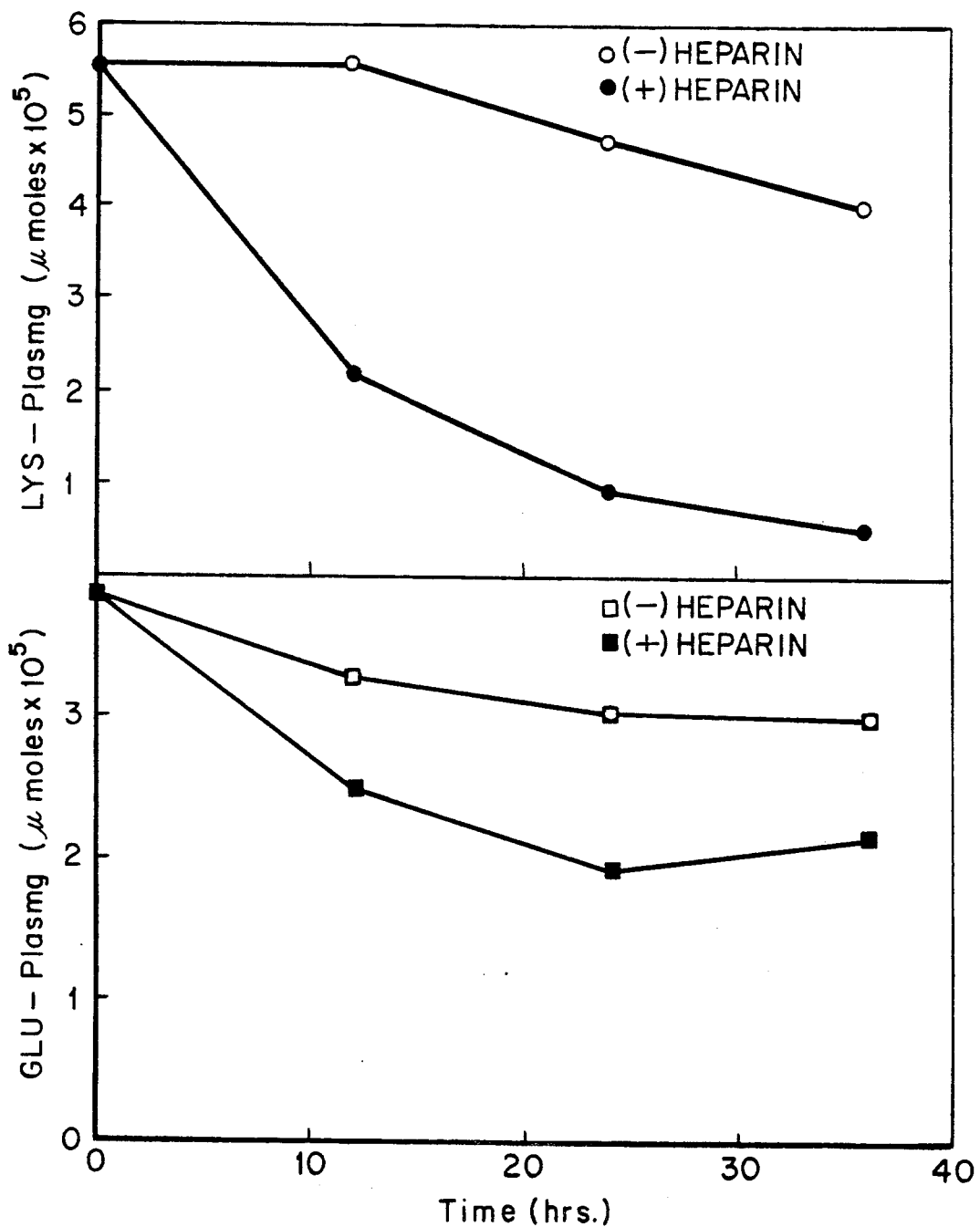
FIG. 6a is a graph showing the effects of HMW-heparin on plasminogen activation by t-PA in the presence or absence of heparin as determined by measuring $^{125}$I-plasminogen consumption with time, as described in Example 4B.

After electrophoresis, the gels were fixed and stained with Coomassie Brilliant Blue R250. Quantitation of plasminogen activation was determined by excising the plasminogen and counting in a gamma counter. The results shown in FIGS. 6a and 6b. FIG. 6a quantitatively shows both Glu and Lys plasminogen activation by t-PA in the presence or absence of unfractionated HMW-heparin by measuring $^{125}$I-plasminogen consumption with time. The results using Lys-plasminogen are shown in the upper panel and the results using Glu-plasminogen are shown in the lower panel.

Figure 6B:
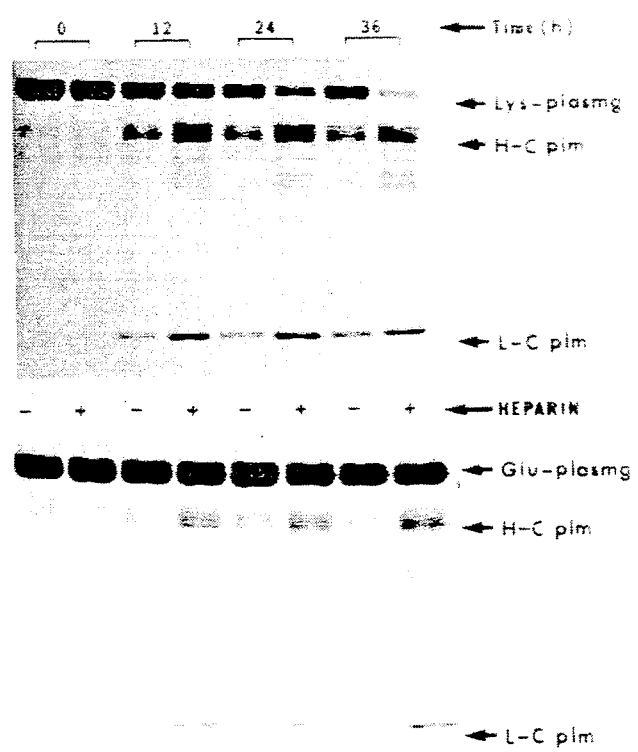
FIG. 6b is a photograph illustrating plasmin production from Gluplasminogen and Lys-plasminogen with (+) and without (−) HMW-heparin, shown by SDS-PAGE with Coomassie Brilliant Blue staining, as described in Example 4B.

FIG. 6b is a photograph showing plasmin production from both Glu and Lys-plasminogen by SDS-PAGE after Coomassie Brilliant Blue Staining with or without HMW-heparin. Plasminogen disappearance is concomitant with the appearance of the heavy chain-plasmin (H-C Plm) and light chain plasmin (L-C Plm). These results show that the production of Glu-plasminogen is slower than Lys-plasminogen, and plasmin generation is greater in the samples containing HMW-heparin. The results are discussed in greater detail in the Biochemistry Paper at page 4036.

Figure 6C:
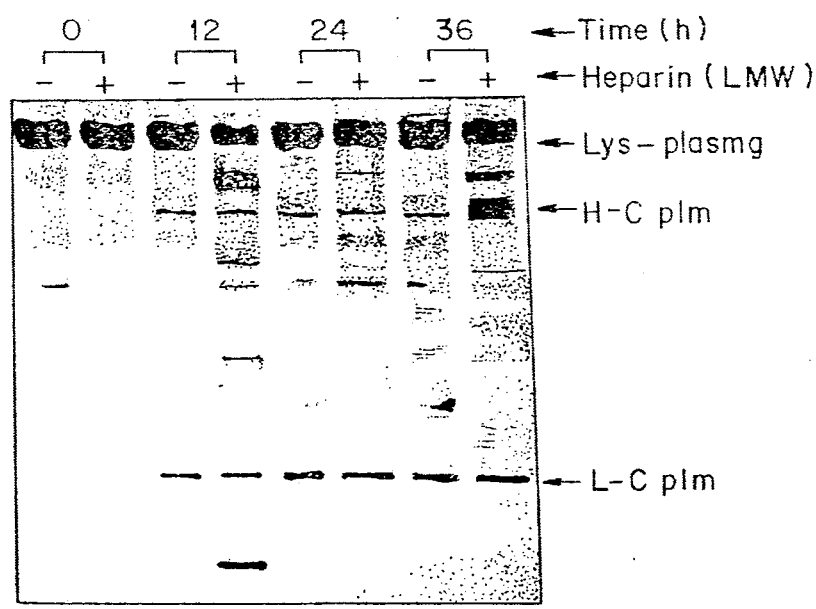
FIG. 6c shows the effect of fractionated LMW-heparin on plasmin production from Lys-plasminogen, shown by SDS-PAGE with Coomassie Blue staining, as described in Example 4C.

4C. The generation plasmin from plasminogen in the presence and absence of LMW-heparin was tested as described in Example 4B, except that only Lys-plasminogen was tested. In this test of LMW-heparin, 4 ug of LMW-heparin corresponded to 1.5 µM of HMW-heparin, the concentration of HMW-heparin which was tested in Example 4B. FIG. 6c is a photograph showing plasmin production from Lys-Plasminogen by SDS-PAGE after Coomassie Brilliant Blue staining with and without LMW-Heparin. The production of plasmin during the period incubation was the same for those samples containing LMW-heparin as for those without LMW-heparin.

The results of this experiment confirmed what was shown in Example 2 with the amidolytic assay. In other words, the LMW-heparin fraction does not stimulate the activity of t-PA and resultant plasmin production in the same manner as observed with the HMW-heparin. As seen on the gel, production of plasmin during the period of incubation was the same for those samples containing LMW-heparin as for those without the LMW-heparin fraction In contrast, the results described in Example 4B showed that plasmin generation was greater in the samples containing HMW-heparin.

EXAMPLE 5

Enhancement of Antithrombin III Inhibition of Thrombin by Heparin

As shown in FIG. 1, Scheme I, heparin works to prevent fibrin clot formation by inhibiting the action of thrombin. Thrombin mediates the transformation of fibrinogen to form a fibrin clot. The anti-coagulant activity of heparin is due, at least in part, to binding of heparin to AT-III. The binding of AT-III increases the inhibitory activity of AT-III towards thrombin as disclosed by Rosenberg et al., J. Biol. Chem., 248, 6490–6505 (1973).

The influence of both HMW and LMW-heparin on the inactivation of thrombin by AT-III was analyzed according to the method described by Teien et al., Thromb. Res., 11, 107–117 (1977).

5A. Thrombin Inhibition by Unfractionated HMW-heparin

At 25° C. 100 µg of calcium and sodium salts of HMW-heparin were each separately mixed with 50 µl of a solution of 0.3 units/ml of AT-III in Tris-EDTA buffer containing 0.05M TRIS-HCl, 7.5 mM EDTA, and 0.17M NaCl pH 8.4. The AT-III was obtained from Kabi Co., Sweden.

After three minutes, a 50 µl solution of thrombin, (10 NIH units thrombin/ml) in 0.15M NaCl, obtained from Sigma was added to each of the HMW-heparin-AT-III mixtures.

After two minutes, 50 µl of 0.3 mM chromogenic thrombin substrate H-d-HHT-Ala-Arg-pNA.20Ac in 0.4 mg/mL polybrene solution was added to each mixture. The chromogenic thrombin substrate was obtained from American Diagnostica, Greenwich, Conn.

A reagent blank was prepared in the same manner as described above, but without the added thrombin.

Amidolysis was assayed for each mixture by following the changing absorbance at 405nm against time for approximately one hour and comparing with the change in absorbance in the reagent blank control described above.

The remaining thrombin activity after thrombin inactivation by heparin and AT-III was determined by the initial rate of hydrolysis ($V_o$), which is defined as a change of absorbance against time. The results of this experiment are displayed in FIG. 7.

5B. Thrombin Inhibition by LMW-Heparin

The influence of the sodium salt of the LMW-Heparin fraction on the inactivation of thrombin by AT-III was analyzed according to the method described in Example 5A.

The results of Examples 5A and 5B are shown in FIG. 7. FIG. 7 compares inhibition of thrombin by AT-III for the sodium (Na+) salts of HMW-heparin and LMW-heparin. FIG. 7 shows that at very low concentrations, the HMW-heparin was slightly more effective than LMW-heparin in stimulating the AT-III mediated inhibition of thrombin. However, both preparations were equally efficient inhibitors at levels below therapeutic concentrations.

EXAMPLE 6

Binding of Heparin to Plasminogen and t-PA, u-PA and AT-III

HMW heparin-agarose and LMW-SEPHAROSE binding studies were performed to determine whether plasminogen, t-PA, or u-PA interact with the LMW-heparin fraction in the same manner which they interact with unfractionated HMW-heparin.

Heparin-agarose having a concentration of 78 μg of heparin/ml of gel was purchased from Sigma Chemical Company, St. Louis, Mo. The binding of the t-PA and u-PA to the heparin-agarose was examined in two ways: (1) by a qualitative method of incubating microgram quantities of protein with the heparin-agarose and analyzing the supernatant (S) and the material bound to the heparin-agarose i.e. the Pellet (P); and, (2) by the quantitative method of incubating the heparin-agarose with various concentrations of radio labeled protein and analyzing the binding in the form of Scatchard Plots.

SCATCHARD PLOT—A Scatchard Plot is a well known means of plotting binding data. It is derived from the following equation:

$$\frac{PX}{X} = \left(\frac{-1}{K_d}\right) + \frac{P_o}{K_d}$$

The reciprocal of the slope of the plotted results is the Kd, where

PX = complex of two molecules
X = free molecule
$P_o$ = binding sites
$K_d$ = equilibrium dissociation constant which measures the affinity of two molecules for each other.

6A. Binding of HMW-Heparin to Plasminogen

Solutions of Glu-plasminogen in a concentration ranging from 4–110 μM, and Lys-plasminogen in a concentration ranging from about 0.1–12 μM, as described in Example 2A, were prepared in binding buffer of 0.1M TRIS-HCl, pH 7.4 at 25° C. Each solution was radiolabelled with $^{125}$I as described in Example 4A. These solutions were incubated with HMW heparin-agarose which contained 3.9 HMW-heparin, based on a concentration of 780 μg of heparin/ml of gel. All experiments were performed by incubating the plasminogen with the HMW-heparin-agarose for 45 minutes. The combined mixture of plasminogen and heparin-agarose were centrifuged with the TRIS-HCl binding buffer described above. The extent of binding of HMW-heparin to labeled plasminogen was determined by measuring the radioactivity of both the supernatant and the extracted pellet and the results were shown on Scatchard Plots. Controls for determining the non-specific binding were performed in an identical manner to that described above, with unsubstituted agarose in place of HMW-heparin-agarose. The results are shown on FIG. 8a and 8b.

Figure 8A:
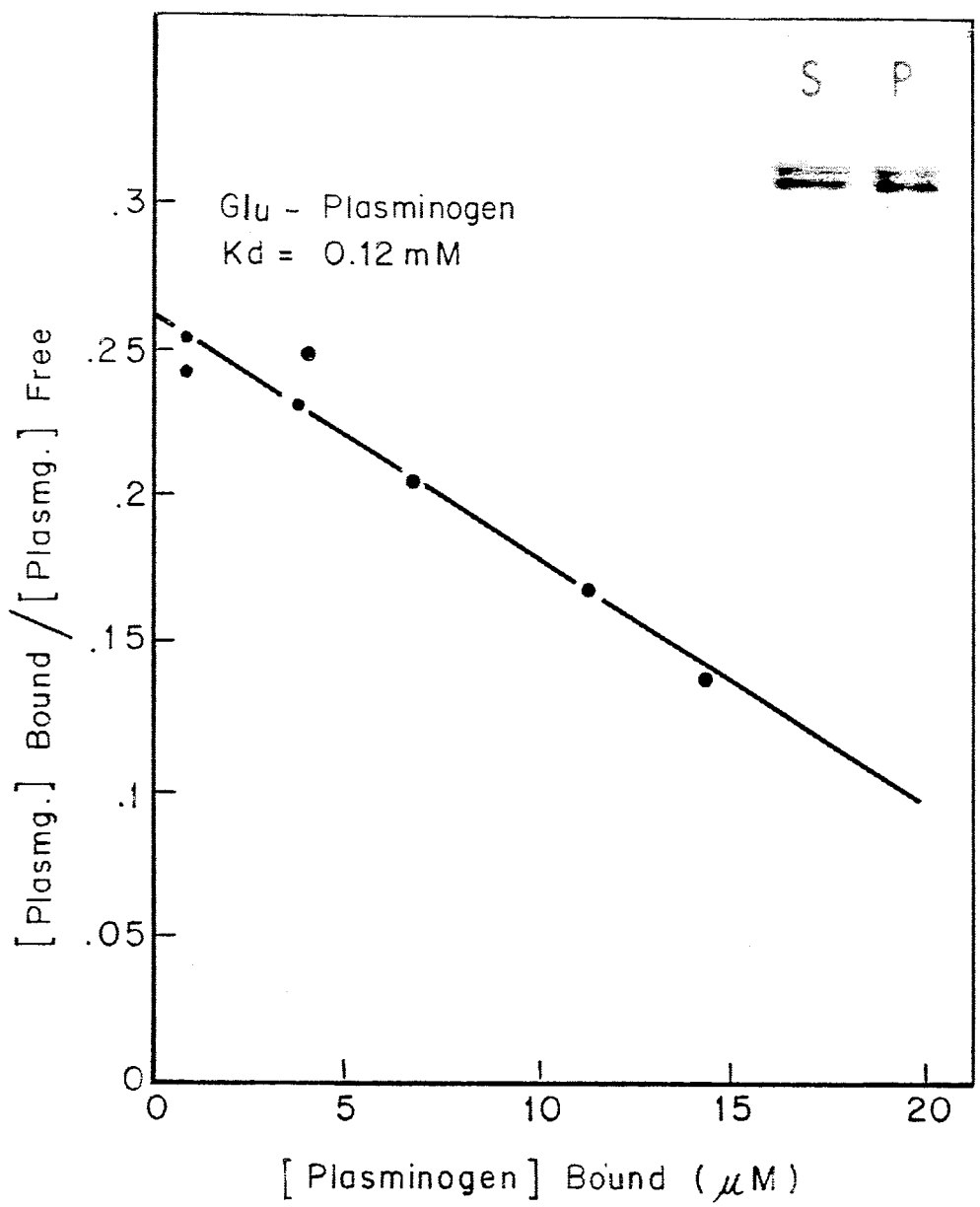
FIG. 8a is a Scatchard Plot which shows the binding of Glu-plasminogen to HMW-heparin agarose, as described in Example 6A. The insert shows the results of SDS-PAGE analysis of bound plasminogen in the pellet (P) and unbound plasminogen in the supernatant (S).
Figure 8B:
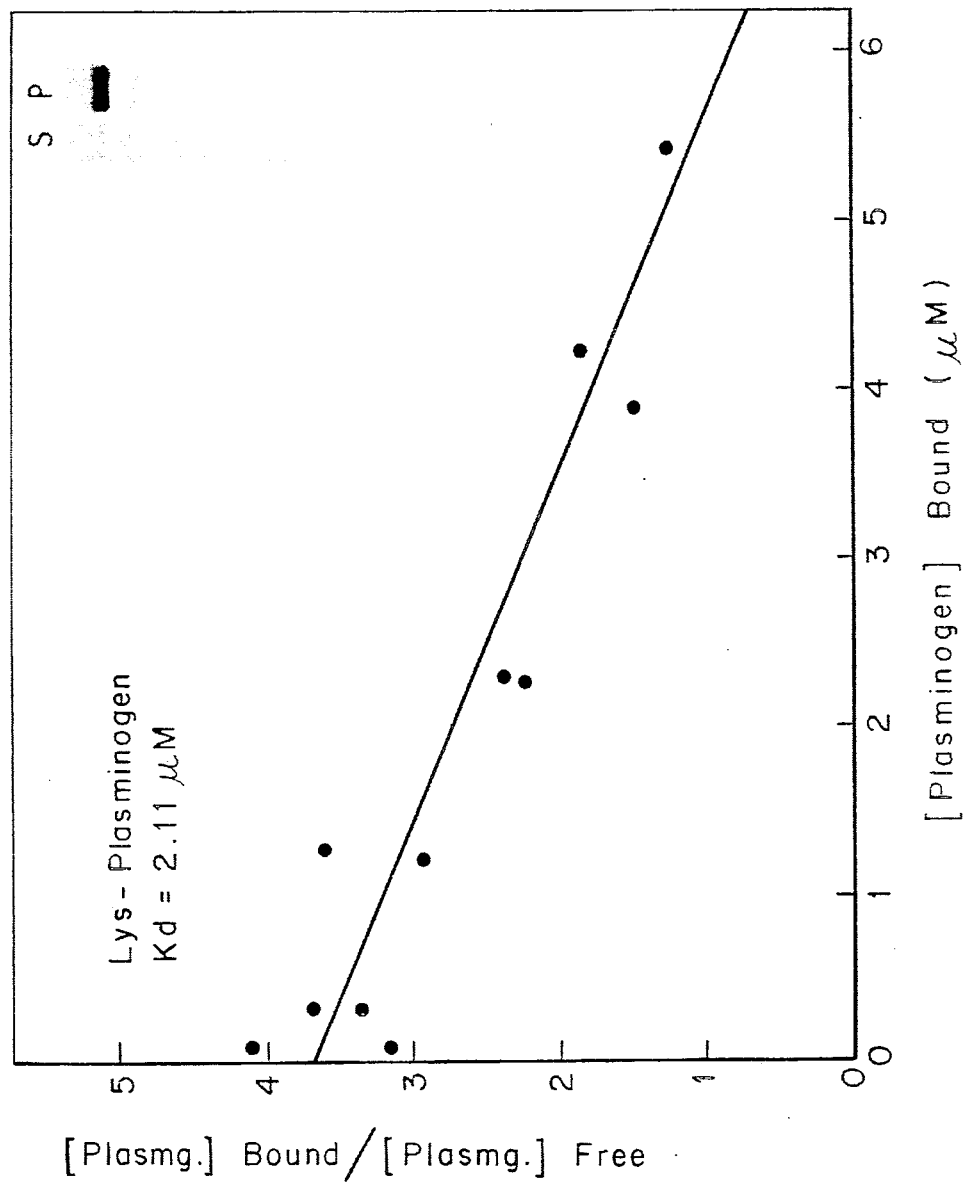
FIG. 8b is a Scatchard Plot which shows the binding of Lys-plasminogen to HMW-heparin agarose, as described in Example 6A. The insert shows the results of SDS-PAGE analysis of bound plasminogen in the pellet (P) and unbound plasminogen in the supernatant (S).

In addition, the molecular forms of plasminogen bound to heparin in the pellet were examined by SDS-PAGE in 8% polyacrylamide-gels. The binding of the plasminogen to the SDS-PAGE is as follows: the bound protein (pellet) was extracted with 0.5 mL of the TRIS-HCl buffer described above. The pellet extract and supernatant were each diluted with 2.0 ml of 2% SDS-20mM dithiothreitol (DTT), and adjusted to 10% TCA. These solutions were then cold centrifuged and the precipitated protein was dissolved in the TRIS-HCl buffer with DTT and applied to 8% SDS polyacrylamide-gels. The inserts to FIGS. 8a and 8b show the results of the SDS-PAGE analysis. (P) represents bound plasminogen from the pellet, and the (S) represents unbound plasminogen from the supernatant.

As shown in FIGS. 8a and 8b Glu-plasminogen was found in both the supernatant (S) and pellet (P) fractions after 45 minutes of incubation with heparin-agarose. In contrast, the Lys-plasminogen shown in FIG. 8b was found only in the pellet (P) indicating that it was fully bound to the HMW-heparin-agarose. This analysis is confirmed by data shown in FIGS. 8a and 8b. These Scatchard Plots show that Glu-plasminogen binds weakly to heparin with a $K_d = 120$ μM, were as Lys-plasminogen binds with a $K_d$ of 2.1 μM, meaning that Lys-plasminogen binds to HMW-heparin 60 times more tightly than does Glu-plasminogen.

6B. Binding of HMW-Heparin to t-PA, u-PA, and AT-III

Binding of HMW-heparin to t-PA, u-PA and AT-III was determined in the same manner described above for plasminogen. The t-PA was the same as described in Example 2A and HMW-heparin-agarose with a concentration of 780 μg of heparin/ml of gel was purchased from Sigma. $^{125}$I-t-PA and $^{125}$I-AT-III had specific activities of 0.9 mCi/mg. $^{125}$I-u-PA had a specific activity of 0.8 Ci/mg. Concentrations were as follows: 0.5–4μM $^{125}$I-t-PA was incubated with 2.0 μM HMW-heparin-agarose; 2.0–12 μM $^{125}$I-AT-III was incubated with 3.9 μM HMW-heparin-agarose; 1.0–7.8 μM, $^{125}$I-u-PA was incubated with 3.9 uM HMW-heparin-agarose.

Figure 9A:
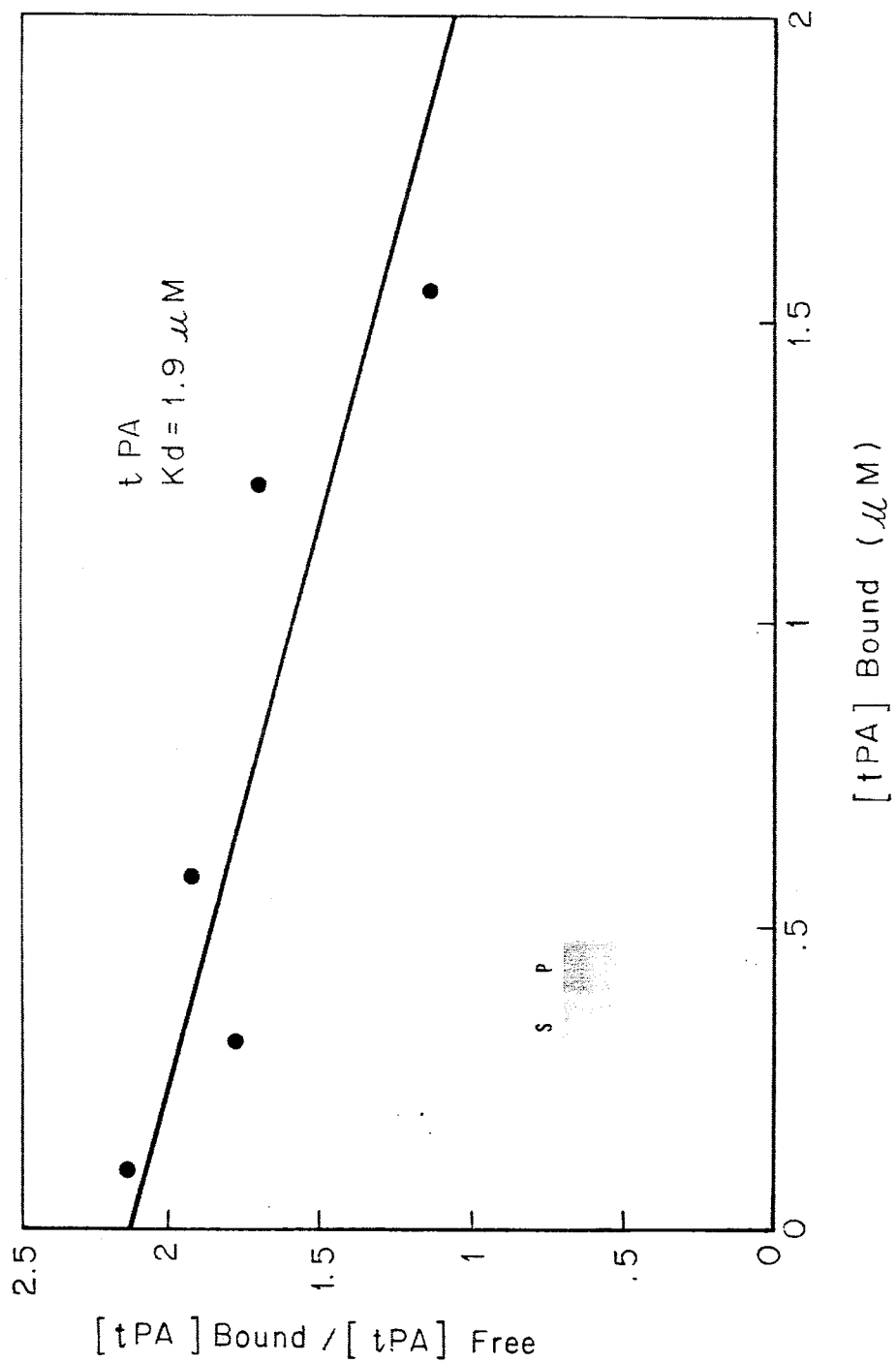
FIG. 9a is a Scatchard Plot which shows the binding of HMW-heparin to t-PA, as described in Example 6B. The insert shows the activity of unbound t-PA in the supernatant (S) and bound t-PA in the pellet (P) after incubation with HMW-heparin-agarose
Figure 9B:
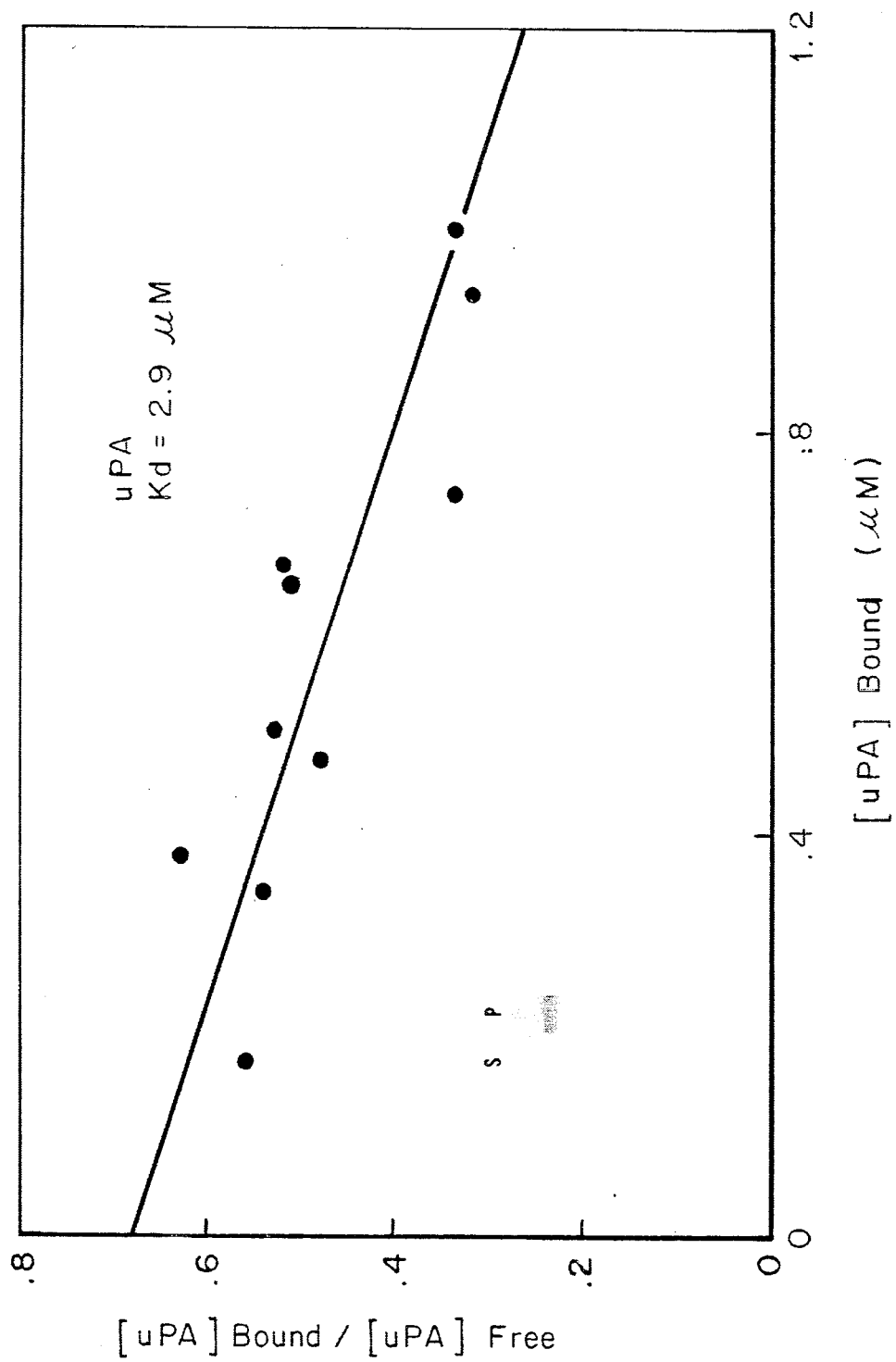
FIG. 9b is a Scatchard Plot which shows the binding of HMW-heparin to u-PA, as described in Example 6B. The insert shows the activity of unbound u-PA in the supernatant (S) and bound t-PA in the pellet (P) after incubation with HMW-heparin-agarose.

The results for t-PA and u-PA are shown in FIGS. 9a and 9b. The inserts to FIGS. 9a and 9b show the activity of t-PA and u-PA, respectively, bound in the supernatant (S) and pellet (P) after incubation with heparin-agarose. The supernatant and pellet samples (S) and (P) were electrophoresed and analyzed by a casein-agar underlay (zymograph) according to the method described by Granelli-Piperno, et al., J. Exp. Med., 148, 223–234 (1978); and Belin et al., EMBO J., 3, 1901–1906 (1984). As shown in FIGS. 9a and 9b, respectively, HMW-heparin binds to t-PA with a $K_d$ of 1.9 μM, and binds to u-PA with a $K_d$ of 2.9 μM. These results suggest, as shown in FIG. 1, Scheme II, that a component of HMW-heparin may serve as a surface which brings plasminogen and t-PA or u-PA together, facilitating and accelerating the conversion of plasminogen to plasmin.

The results of the binding of HMW-heparin to radioiodinated AT-III ($^{125}$I-AT-III) showed a $K_d$ for the HMW-heparin-AT-III of 16 μM. (Scatchard Plot not shown)

6C. Binding of LMW-heparin to Plasminogen, t-PA, u-PA and AT-III

To determine whether t-PA, u-PA, Glu- or Lys-plasminogen interact with the LMW-heparin fraction in the same manner described in Example 6A and 6B for the HMW-heparin, the following binding studies were performed using insoluble LMW-heparin-SEPHAROSE in the same manner specified in Example 6A for HMW-Heparin-agarose.

Immobilization of the LMW-heparin on to SEPHAROSE was carried out by CNBr activation according to the method of Smith, et al., Analytical Biochemistry, 109, 466-473 (1980), as follows: 250 mg LMW-heparin was dissolved in 16 mL of ice-cooled $dH_2O$ which was adjusted to a pH of 7.8. The solution was stirred and one gram of CNBr was added. After the CNBr was completely dissolved, 15 ml of washed SEPHAROSE 4B was added to the solution. This solution was maintained at a pH of 11 for 25 minutes by the addition of 6M NaOH to form a suspension. The suspension was allowed to stir overnight at room temperature. After twenty-four hours, the gel was filtered and washed in a sintered glass funnel with 400 mL of $dH_2O$. Excess reactive groups were blocked by reacting with 1M ethanolamine at a pH of 9.0 for three hours. The LMW-heparin-SEPHAROSE was then washed sequentially with solutions of 150 ml $dH_2O$; 100 ml 0.1M NaAc, pH of 4.7; 100ml 0.5M Na $HCO_3$; and, 400ml $dH_2O$. The resulting gel was stored with 0.02% Na Azide at 4° C. until it was used.

The amount of LMW-heparin covalently coupled to SEPHAROSE was determined colorimetrically using the properties of the metachromatic dye, toluidine blue as described by Smith et al., *Anal. Biochem.*, 109, 466-473 (1980). Although this method was specifically directed towards HMW-heparin, we adapted the method to determine the concentration/amount of LMW-heparin bound to SEPHAROSE. This method requires monitoring the dye depletion in the supernatant by observing the change in absorbance at the 631 nm wavelength, as the toluidine blue is absorbed onto the LMW-heparin-SEPHAROSE. A graph of $\mu$l settled gel vs. Absorbance at 631 nm was then prepared as shown in FIG. 10a, and the results were correlated with a standard curve, FIG. 10b, which we previously prepared by plotting $\mu$g LMW-heparin vs. absorbance at 631 nm.

Studies on the binding of LMW-heparin-SEPHAROSE to plasminogen, u-PA, t-PA, and AT-III were done in the same manner described in Examples 6A and 6B for HMW-heparin-agarose. As in Example 6A, the results were analyzed by Scatchard Plots, as well as qualitatively by using SDS-gel electrophorese to visualize the plasminogen, u-PA, t-PA, or AT-III bound to LMW-heparin-SEPHAROSE in the pellet (P) and unbound in the supernatant (S). The results are shown in FIGS. 11a (plasminogen) 11b (u-PA), 11c and 11d (AT-III). Since the LMW-heparin fraction does not significantly bind to t-PA, a Scatchard for t-PA could not, of course, be provided.

As shown in FIG. 11a, Lys-plasminogen binds to the LMW-heparin fraction with a dissociation constant, $K_d$ of 32 $\mu$M, a fairly weak binding strength. This binding strength represents a value which is 15-fold weaker than that obtained with HMW-heparin in Example 6A (see FIG. 8b) which has a $K_d$ of 2.11 $\mu$M. In contrast to the binding of Lys-plasminogen, Glu-plasminogen did not exhibit any measurable binding to the LMW-heparin. This lack of binding of the Glu-plasminogen to LMW-heparin is evidenced by its quantitative presence in the supernatant (S), and its absence in the pellet (P) (see insert to FIG. 11a). The binding studies of t-PA to LMW-heparin have shown that over the range of concentrations used in these experiments, ranging from about 0.5-4.0 $\mu$M, the binding strength was never more than that found for the unsubstituted agarose control, i.e., 5% of the total protein, which corresponds to non-specific binding (see FIG. 11b). The results shown in FIG. 11b illustrate that t-PA has very little or no affinity for the LMW-heparin-SEPHAROSE preparation.

Figure 11C:
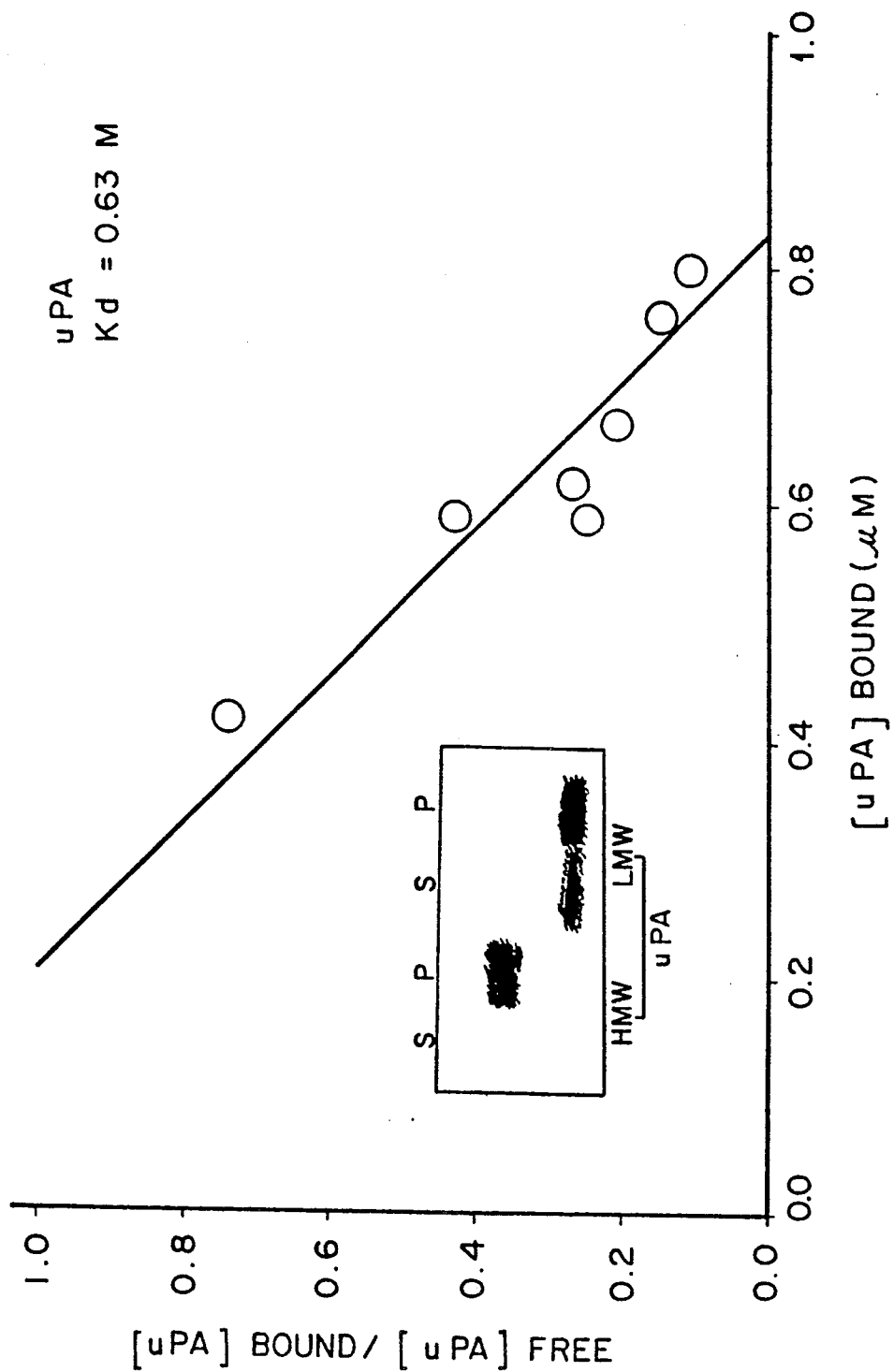
FIG. 11c is a Scatchard Plot of LMW-heparin binding to u-PA, as described in Example 6C. The insert represents the activity of unbound u-PA in the supernatant (S) and bound u-PA in the pellet (P) after incubation with LMW-heparin-SEPHAROSE and HMW-SEPHAROSE, respectively.

In contrast to the binding of t-PA, u-PA bound tightly to the LMW-heparin fraction, exhibiting a binding constant, $K_d$ of 0.63 $\mu$M (see FIG. 11c). The slight stimulation of the u-PA activity by LMW-heparin shown in Example 2B and graphically illustrated in FIG. 3c is consistent with these results. The increase in activity might have been greater if LMW-heparin were able to bind to either u-PA or to plasminogen. These results suggest that binding of LMW-heparin to both plasminogen and plasminogen-activators (-PA's) might be necessary for maximal enhancement of plasminogen activation. In the binding studies of LMW-heparin and AT-III, the results indicated that LMW-heparin binds to AT-III.

The anticoagulant activity of heparin is mediated by its binding to AT-III, which thereby stimulates the ability of AT-III to inhibit the clotting proteases. As shown in Example 5B, above, the anti-coagulant activity of both HMW-heparin and LMW-heparin is retained. It was therefore important to demonstrate that AT-III does, in fact, bind to LMW-heparin. The results of the binding studies of AT-III to LMW-heparin-SEPHAROSE are shown in FIG. 11d. These results show that the interaction between LMW-heparin and AT-III occurs with a binding strength, $K_d$ of 3.2 $\mu$M. Accordingly, the LMW-heparin fraction retains the anti-coagulant properties of HMW-heparin by maintaining the ability to bind with a high affinity to AT-III.

EXAMPLE 7

Separation and Isolation of a La-Heparin Fraction

7A. Isolation Of Heparin-Agarose

In order to fractionate heparin on a t-PA-SEPHAROSE gel filtration matrix column, the binding sites on t-PA which react with heparin must be protected when the t-PA is bound to the activated SEPHAROSE gel filtration matrix. The t-PA binding sites for heparin were protected by binding the t-PA to the SEPHAROSE in the presence of heparin. Heparin, however, contains a plurality of free amino groups, see FIG. 2, which could covalently bind to activated SEPHAROSE. The binding of heparin to the activated SEPHAROSE was prevented by acetylating the amino groups of heparin by the following procedure.

Unfractionated-heparin-agarose was acetylated by following the procedures described by Danishefsky et al., in *Biochem. Biophys. Acta*, 101, 37-45 (1965) with the variations described below. 15 ml of heparin-agarose 780$\mu$g heparin/ml gel volume obtained from Sigma was washed three times with 10% MeOH, and 5ml of 10% MeOH was then added to this washed and packed gel preparation. The gel was then cooled to 4° C. and stirred in a spinner bottle. The pH of the gel was adjusted by adding $NaCO_3$ until a pH of 9.1 was reached. Subsequently, 100 $\mu$l reagent grade acetic anhydride, purchased from Fisher Scientific International, Pittsburgh, PA was added in 20 microliter fractions over a period of 30 minutes, and NaCO₃ was added as necessary to maintain the pH at 7.0.

After one hour, the gel was checked for free amino groups using trinitro benzene sulfuric acid (TNBS) in a saturated borate solution. The gel which was not pre-treated with acidic anhydride turned reddish-yellow upon addition of TNBS. The gel which was pre-treated with acidic anhydride, however, remained clear upon addition of TNBS. The gel was washed with 100 µl of dH₂O and 100 µl of 0.5 NaCl. The gel was stored in 0.5M NaCl.

7B. Binding Of rt-PA To Acetylated Heparin-Agarose

In order to determine whether the acetylation of the free amino groups of heparin, prepared in Example 7A, destroyed the heparin binding sites for the recombinant t-PA ("rt-PA") or whether heparin binds to the rt-PA at sites other than its amino groups, the binding of rt-PA to acetylated heparin was compared to the binding of unmodified heparin on SDS-polyacrylamide slab gels. Twenty (20) µl acetylated heparin-agarose prepared in Example 7A and 20 µl of non-acetylated heparin-agarose were both incubated for 45 minutes at room temperature after the addition of 10 µl of 0.2 µg/ml solution of rt-PA, obtained from Genentech, Palo Alto, Calif. The extent of binding of the rt-PA to the heparin-agarose fractions was determined by visualizing the bound fraction in the pellet, and the unbound fraction in the supernatant on 8% SDS-polyacrylamide slab gels. The rt-PA activity was assayed by casein-agar underlay (zymograph), according to the method of Granelli-Piperno et al., *J. Exp. Med.*, 148, 223–224 (1978); and, Vassalli et al., *J. Exp. Med.*, 159, 1653–1668 (1984), the results are shown in FIG. 12.

Figure 12:
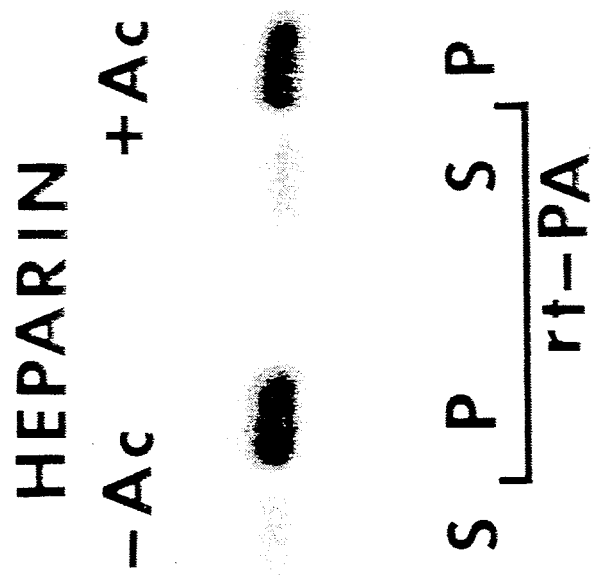
FIG. 12 is a zymograph showing the binding of rt-PA to unfractionated acetylated heparin, vs. unfractionated, unmodified heparin, as described in Example 7B.

In FIG. 12, the bands represent rt-PA activity on the casein-agar underlay, showing that acetylated heparin and unmodified heparin exhibit similar binding characteristics to rt-PA, and thus proving that the acetylation of heparin does not prevent the binding of heparin to t-PA. 7C. Acetylation Of Heparin.

The acetylation of heparin was performed in the same manner described in Example 7A. The sodium (Na⁺) salt of heparin obtained from Sigma was utilized for this experiment. Samples of the heparin were tested for free amino groups by thin layer paper chromatography (TLPC) and spraying with ninhydrin which tests for free amino groups in sugars. Free amino groups, however, were not detected.

7D. Preparation Of rt-PA-SEPHAROSE rt-PA obtained from Genentech at a concentration of 15 mg/vial was coupled to CNBr-activated SE-PHAROSE, obtained from Pharmacia, Sweden. The coupling of the rt-PA was performed in the presence of the acetylated heparin, prepared in Example 7C, in order to protect the heparin binding sites of the rt-PA.

A coupling procedure recommended by Pharmacia was modified as follows: 10 mg of rt-PA was dissolved in 10 ml of 0.2M HEPES, and 5% glycerol pH 7.4. Two (2) grams of packed Tresyl-SEPHAROSE was washed with 1 mM HCl, and then added to the 10 ml rt-PA solution. The mixture was rotated at 4° C. overnight and then rotated for one hour at room temperature.

Excess ligand (rt-PA and acetylated heparin which had not bound to the SEPHAROSE) was washed with the above-described solution, and the remaining active groups of the Tresyl-activated SEPHAROSE were blocked with 0.1M Tris-HCl buffered at a pH of 8 for 4 hours. The acetylated heparin was removed by washing the gel with 0.1M Acetate buffer solution at a pH 4 containing 0.5M NaCl followed by 0.1M Tris, 0.5M NaCl pH 8.0.

This procedure coupled 0.7 mg of rt-PA/ml of SEPHAROSE gel.

7E. Fractionation Of Heparin On The rt-PA SEPHAROSE Column

Figure 13:
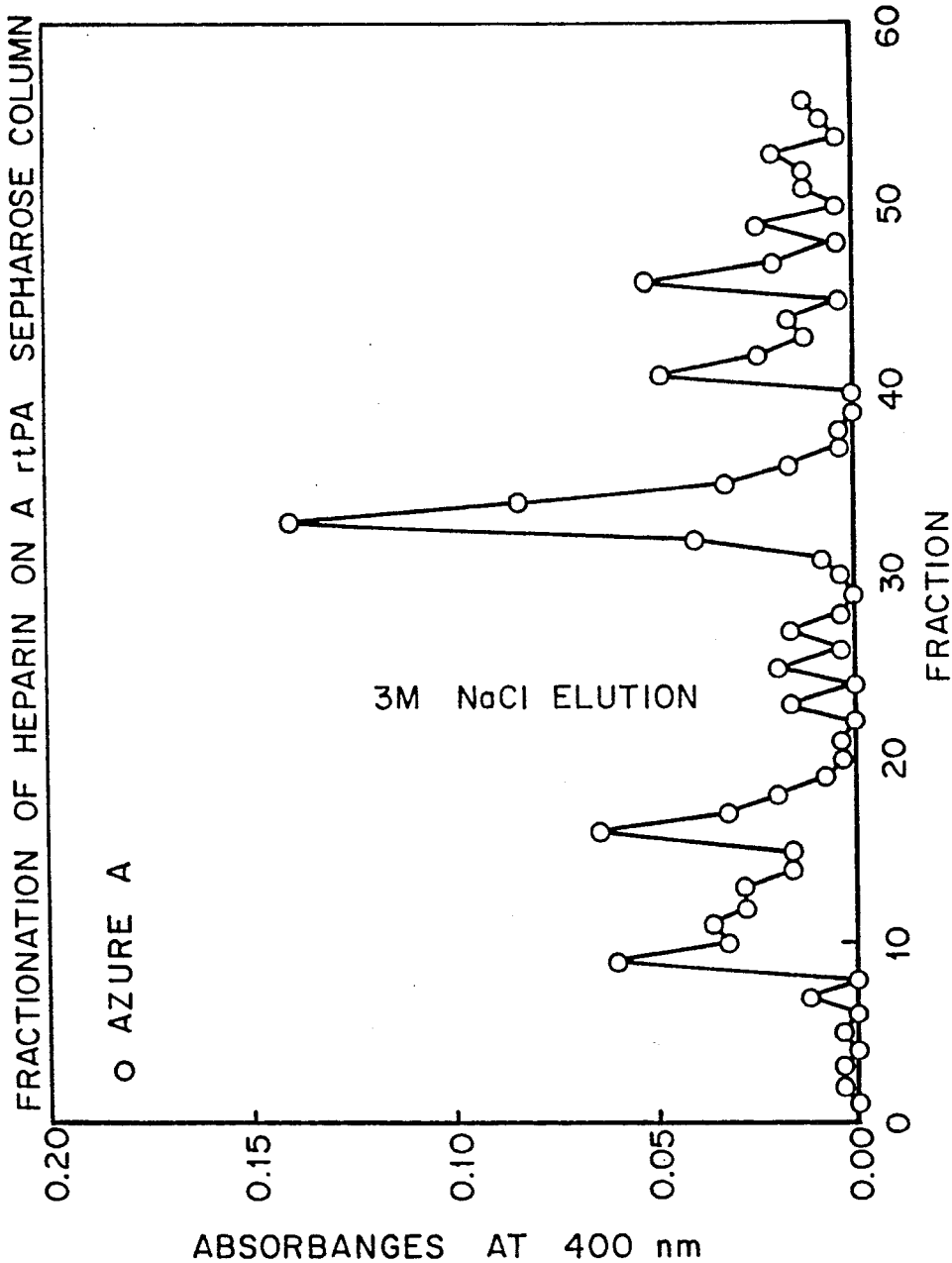
FIG. 13 is a graph showing the absorbance at 490 nm of LA-heparin fractions and HA-heparin fractions separated on a rt-PA-SEPHAROSE column, as described in Example 7E. The HA-heparin fractions were separated from the column by eluting with 3M NaCl solution.

The Na⁺ salt of heparin (unacetylated) obtained from Sigma was fractionated on the basis of its affinity for the immobilized rt-PA. The fractionation was carried out at 4° C. on an 8 ml rt-PA column made from the rt-PA-SEPHAROSE prepared in Example 7C. 200 µg heparin was added to the column at a flow rate of 1.0 ml/min at 4° C. and 1 ml fractions were collected. The column was then washed with three column volumes with 0.1M Tris-HCl pH 7.4 to elute any low affinity heparin (LA-heparin) remaining in the column. Bound heparin was then eluted with 0.1M Tris-HCl 2.5M NaCl. The high affinity fractions (HA-heparin) collected with the 2.5 NaCl were dialyzed against H₂O, lyophilized and resuspended in 0.1M Tris, pH 7.4. The concentrations of the fractions were determined by a modified Azure A method to determine their absorbance at 490 nm as described by Jaques et al. in *Physiol. Pharmacol.*, 45, 787–94 (1967), the results of which are shown in FIG. 13.

EXAMPLE 8

Influence of Heparin Fractionated on rt-PA-SEPHAROSE on the Inactivation of Thrombin by Antithrombin III (AT-III)

The LA-heparin fractions obtained in Example 7E were compared with unfractionated heparin to determine whether they have retained their ability to stimulate the inactivation of thrombin by AT-III, and thus retained their anti-coagulant activity.

Figure 14:
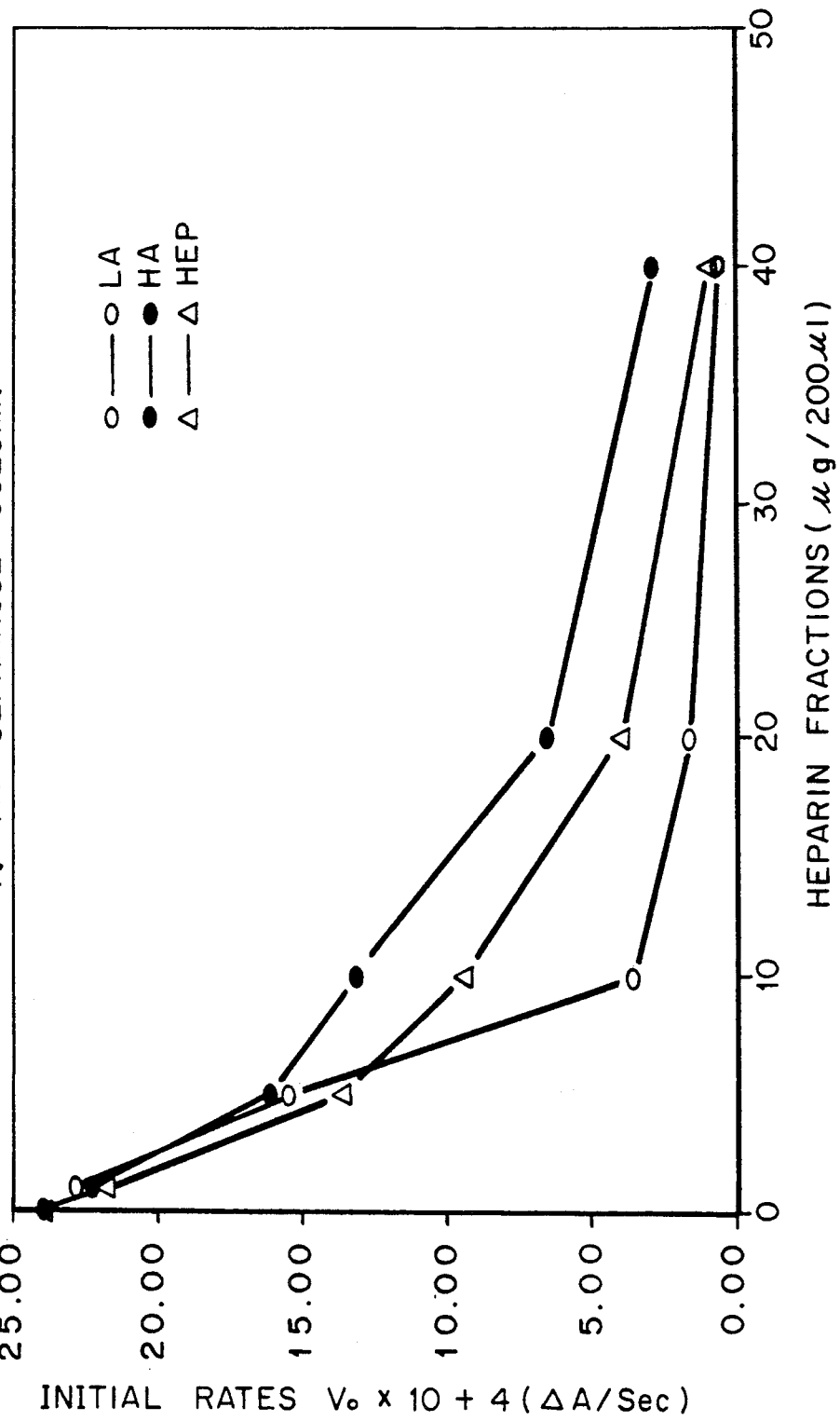
FIG. 14 is a graph comparing the initial rates of hydrolysis by a thrombin/AT-III mixture in the presence of unfractionated HMW-heparin, LA-heparin and HA-heparin fractions, as described in Example 8.

Three heparin fractions, 50 ng each, of LA-Heparin, HA-heparin, obtained in Example 7D, and unfractionated HMW-heparin were each mixed with 50 µl of AT-III having a concentration of 0.3 unit/ml, in a Tris-EDTA buffer which is made up of 0.05M Tris-HCl, 7.5 mM EDTA and 0.17M NaCl pH 8.4. After 3 minutes, 50 µl thrombin, in a concentration of 10 NIH units/ml, and 0.15 M NaCl was added to each heparin-AT-III mixture. After 2 minutes, 50 ul of the chromogenic thrombin substrate H-D-HHT-Ala-Arg-pNA.20Ac, 0.3 mM concentration in 0.4 µg/ml polybrene solution was added to each mixture. Amidolysis was then assayed by observing a change in absorbance at 405 nm over time. The thrombin activity remaining after inactivation by each of the heparin +AT-III mixtures was determined by the initial rates of hydrolysis (V₀), the results are shown in FIG. 14. FIG. 14 shows that especially at low concentrations, LA-heparin, HA-heparin fractions and unfractionated HMW-heparin are all effective in stimulating the inactivation of thrombin by AT-III. In fact, at low concentrations, i.e., 10 µg/200 µl, LA-heparin showed a higher anti-clotting activity than HMW-heparin. Accordingly, this experiment proves that the LA-heparin fraction retains its anti-coagulant activity.

EXAMPLE 9

Effects of Plasminogen Activation by Heparin Fractionated on rt-PA-SEPHAROSE

The ability of the HA and LA-heparin fractions prepared as described in Example 7E, to stimulate amidolytic plasmin activity of lys-plasminogen in the presence of t-PA was determined, as described in Example 2A. The results of this experiment are shown in FIG. 15.

Figure 15:
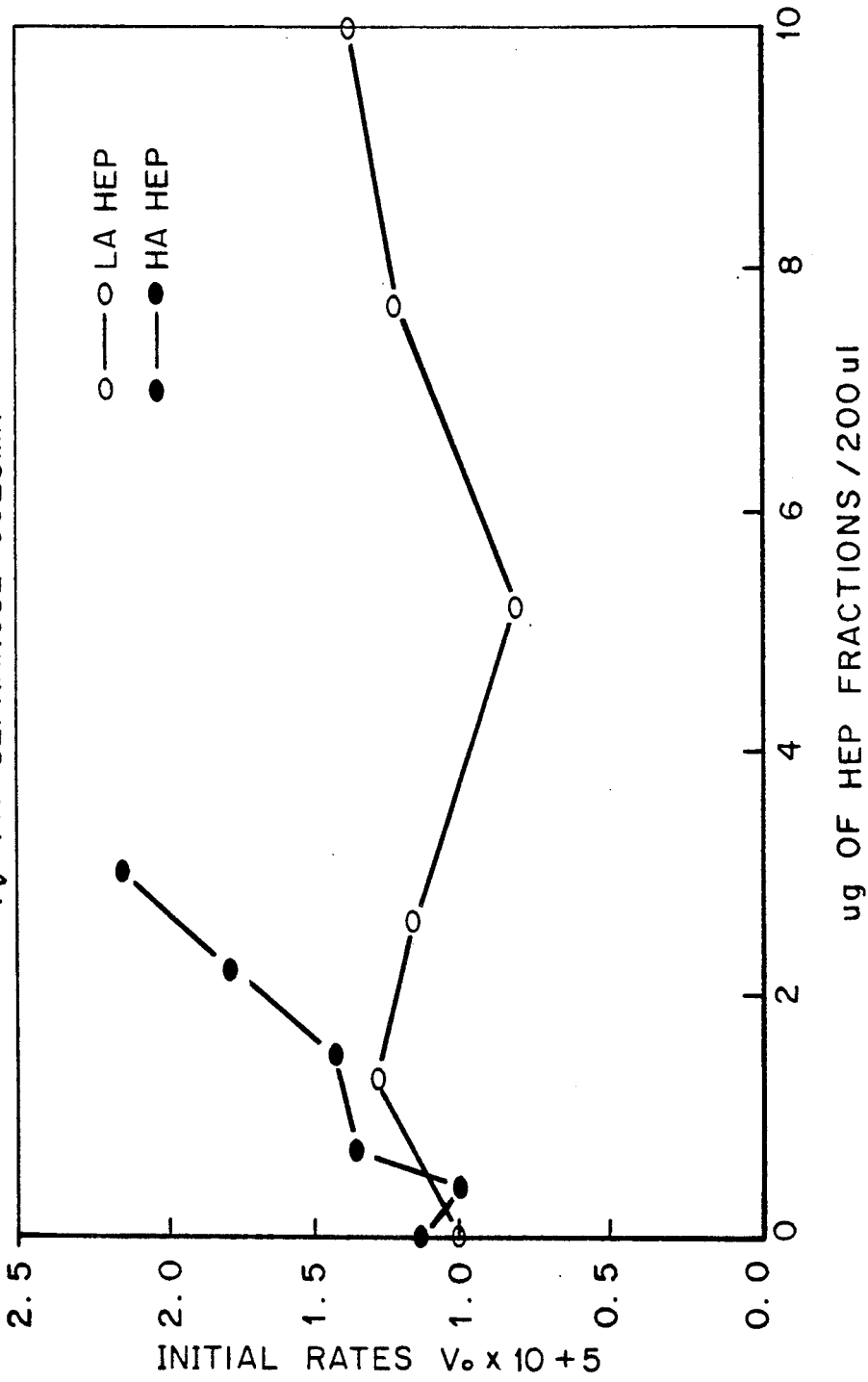
FIG. 15 is a graph comparing the initial rates of hydrolysis by t-PA in the presence of LA-heparin and HA-heparin fractions, illustrating the differences in rates of plasminogen activation by t-PA in the presence of the respective heparin fractions, as described in Example 9.

FIG. 15 shows that at the heparin concentration assayed, a marked increase in stimulation of the amidolytic plasmin activity of plasminogen in the presence of t-PA by the HA-heparin fraction was observed. However, when the LA-heparin fractions were assayed, almost no increase in stimulation was observed. These results prove that the LA-heparin fractions exhibit no stimulatory effect in contrast to the high stimulatory effect observed for the unfractionated heparin on plasminogen activation in the presence of t-PA. Moreover, the HA-heparin fractions show a marked increase over unfractionated heparin in the stimulation of plasminogen activation in the presence of t-PA.

EXAMPLE 10

Fractionation of Heparin Based on Its Affinity Towards u-PA, Glu-, or Lys-Plasminogen Unfractionated heparin samples are fractionated on separate u-PA-SEPHAROSE, Glu-plasminogen-SEPHAROSE and lys-plasminogen-SEPHAROSE columns, respectively, as described in Example 7. The respective low affinity heparin fractions retain their anti-coagulant activity but do not enhance plasminogen activation in the presence of u-PA, or t-PA, respectively, assayed as described in Examples 8 and 9.

Thus, while we have described what are presently believed to be the preferred embodiments of the present invention, other and further changes and modifications can be made thereto without departing from the true scope of the invention, and it is intended to claim all such changes and modifications.

We claim:

1. A LA-heparin composition lacking affinity for t-PA which has been isolated on the basis of its lack of affinity to t-PA by a process which comprises:
    (a) immobilizing t-PA on a solid medium which includes a gel filtration matrix; and
    (b) eluting heparin past the immobilized t-PA to isolate heparin fractions having a low affinity for the immobilized t-PA,
wherein step (a) of the process further comprises:
    protecting the heparin binding sites on t-PA by combining t-PA with heparin; and
    removing the heparin from the gel filtration matrix immobilized t-PA.

2. A composition for thrombolytic therapy comprising:
    (i) t-PA;
    (ii) a heparin composition lacking affinity for a t-PA which has been isolated on the basis of its lack of affinity to t-PA; and
    (iii) a therapeutically effective carrier,
    wherein said LA-heparin has been isolated by the process comprising:
        (a) immobilizing t-PA on a solid medium which includes a gel filtration matrix; and
        (b) eluting heparin past the immobilized t-PA to isolate heparin fractions having a low affinity for the immobilized t-PA,
    wherein step (a) of the process further comprises:
    protecting the heparin binding sites on t-PA by combining t-PA with heparin; and
    removing the heparin from the gel filtration matrix immobilized t-PA,
    whereby the t-PA dissolves blood clots while the heparin composition prevents reocclusion without the side effects of HMW-heparin which stimulates the t-PA activity and reduces the specificity of t-PA's fibrinolytic activity.

3. A composition for thrombolytic therapy comprising:
    (a) t-PA;
    (b) a LMW-heparin composition which was prepared by nitrous acid depolymerization of HMW-heparin, and selected as the fraction having an average molecular weight from about 3,000 to about 8,000 daltons, an anti-XA activity greater than about 150 U/mg and an APTT greater than 40 IU/mg; and
    (c) a therapeutically effective carrier,
        whereby the t-PA dissolves blood clots while the LMW-heparin composition prevents reocclusion without the side effects of HMW-heparin which stimulates the t-PA activity and reduces the specificity of t-PA's fibrinolytic activity.

4. A method of thrombolytic therapy which comprises:
    administering a dose of a LMW-heparin composition prepared by nitrous acid depolymerization of HMW-heparin, and selected as a fraction having an average molecular weight from about 3,000 to about 8,000 daltons, an anti-XA activity greater than about 150 U/mg and an APTT greater than 40 IU/mg, and
    administrating t-PA, whereby reocclusion does not occur and t-PA activity is not stimulated, and fibrinolytic activity is not interfered with by the heparin composition.

* * * * *